US009719144B2

(12) United States Patent
Krajmalnik-Brown et al.

(10) Patent No.: US 9,719,144 B2
(45) Date of Patent: Aug. 1, 2017

(54) MICROBIOME MARKERS AND THERAPIES FOR AUTISM SPECTRUM DISORDERS

(71) Applicant: Arizona Board of Regents, Scottsdale, AZ (US)

(72) Inventors: Rosa Krajmalnik-Brown, Chandler, AZ (US); Dae-Wook Kang, Phoenix, AZ (US); Jin Gyoon Park, Phoenix, AZ (US); Joshua Labaer, Chandler, AZ (US); Zehra Ilhan, Tempe, AZ (US)

(73) Assignee: ARIZONA BOARD OF REGENTS, Scottsdale, AZ (US)

( * ) Notice: Subject to any disclaimer, the term of this patent is extended or adjusted under 35 U.S.C. 154(b) by 0 days.

(21) Appl. No.: 14/403,425

(22) PCT Filed: Mar. 15, 2013

(86) PCT No.: PCT/US2013/032668
§ 371 (c)(1),
(2) Date: Nov. 24, 2014

(87) PCT Pub. No.: WO2013/176774
PCT Pub. Date: Nov. 28, 2013

(65) Prior Publication Data
US 2015/0152484 A1 Jun. 4, 2015

Related U.S. Application Data

(60) Provisional application No. 61/651,846, filed on May 25, 2012.

(51) Int. Cl.
*A61K 35/741* (2015.01)
*C12Q 1/68* (2006.01)
*G01N 33/68* (2006.01)
*A61K 31/437* (2006.01)

(52) U.S. Cl.
CPC ............ *C12Q 1/689* (2013.01); *A61K 31/437* (2013.01); *A61K 35/741* (2013.01); *C12Q 1/6883* (2013.01); *G01N 33/6896* (2013.01); *C12Q 2600/142* (2013.01); *C12Q 2600/158* (2013.01)

(58) Field of Classification Search
None
See application file for complete search history.

(56) References Cited

U.S. PATENT DOCUMENTS

2004/0170617 A1 9/2004 Finegold
2011/0091431 A1 4/2011 Olmstead

OTHER PUBLICATIONS

Fogarty et al., Comparison of Bacteroides-Provetella 16S rRNA Genetic Markers for Fecal Samples from Different Animal Species, Applied and Environmental Microbiology, Oct. 2005, p. 5999-6007.*
Adams et al., "Gastrointestinal flora and gastrointestinal status in children with autism—comparisons to typical children and correlation with autism severity" Bmc Gastroenterol , 2011, 11:22, 1-13.
Adams et al., "Mercury in first-cut baby hair of children with autism versus typically-developing children" Toxicological and Environmental, 2008, 90:4, 739-753.
Arumugam et al., "Enterotypes of the human gut microbiome" Nature, 2011, 473, 174-180.
Atarashi et al., "Induction of Colonic Regulatory T Cells by Indigenous Clostridium Species" 331, Science, 2011, 337-341.
Berg, "The indigenous gastrointestinal microflora" Trends Microbial, 1996, 4, 430-435.
Borriello, "Clostridial Disease of the Gut" Clinical Infectious Diseases, 1995, 20, S242-S250.
Bryant et al., "Bacteroides *Ruminicola* n. sp. and the New Genus and Species Succinimonas Amylolytica" Journal of Bacteriol, 76, 15-23, 1958.
Buie et al.,"Evaluation, Diagnosis, and Treatment of Gastrointestinal Disorders in Individuals With ASDs: A Consensus Report", Pediatrics, 125, S1-S18, (2010).
Chao et al., "Estimating the Number of via Sample Coverage" Journal of the American Statistical Association, 1992, 87:417, 210-217.
Cole et al., "Pyschological Risk Factors for HIV Pathogenesis: Mediation by the Autonomic Nervous System", Society of Biological Psychiatry, 2003, 54, 1444-1456.
J.R. Cole et al., "The Ribosomal Database Project: improved alignments and new tools for rRNA analysis", Nucleic Acids Research, 2008, 37, D141-D145.
Collins & Bercik, "The Relationship Between Intestinal Microbiota and the Central Nervous System in Normal Gastrointestinal Function and Disease" Gastroenterology, 2003 (2009), 136:6.
Darrien et al., "Akkermansia muciniphila gen. nov., sp. nova., a human intestinal mucin-degrading bacterium" International Journal of Systematic and Evolutionary Microbiology, 2004, 54, 1469-1476.

(Continued)

*Primary Examiner* — Suzanne M Noakes
*Assistant Examiner* — Stephen Chong
(74) *Attorney, Agent, or Firm* — Nixon Peabody LLP

(57) ABSTRACT

The present disclosure provides for characterization of normal flora and identifying biomarkers in the gut of healthy, neruotypical subjects. Aspect of the disclosure provide for the characterization of the gut microbiome in ADS subjects, characterized by reduced richness and significant loss of the '*Prevotella*-like enterotype' compared to neurotypical subjects. The relative abundance of genera *Prevotella, Coprococcus*, Prevotellaceae and Veillonellaceae are significantly lower in autistic children than in neurotypical children. Further, *Prevotella*, is one of the three main classifiers for the human enterotypes, along with *Bacteroides* and *Ruminococcus*. These three core genera are among main contributors in the principle component analysis. '*Prevotella*-like enterotype' was absent in the autistic group, while neurotypical samples showed an even distribution among the three enterotypes. The present disclosure provides for an understanding the association between gut microbiota, health, and disease states, and provides for potential diagnostic and therapeutic targets.

14 Claims, 12 Drawing Sheets

(56) References Cited

OTHER PUBLICATIONS

Filippo et al., "Impact of diet in shaping gut microbiota revealed by a comparative study in children from Europe and rural Africa" PNAS, 107:33, 14691-14696.
Magistris et al., "Alterations of the Intestinal Barrier in Patients With Autism Spectrum Disorders and in Their First-degree Relatives", Gastroenterology, 2010, 51:4, 418-424.
Deufemia et al., "Abnormal intestinal permeability in children with autism" Acta Pediatric, 1996, 85: 1076.
Dieterle et al., "Renal biomarker qualification submission: a dialog between the FDA-EMEA and Predictive Safety Testing Consortium" Nature Biotechnology, 2010, 28:5, 455-462.
Dorn et al., "Invasion of Human Oral Epithelial Cells by Prevotella intermedia" 1998,66:12, 6054-6057.
Duncan et al., "Acetate Utilization and Butyryl Coenzyme A (CoA):Acetate-CoA Transferase in Butyrate-Producing Bacteria from the Human Large Intestine" Applied and Environmental Microbioloay, 2002, 68:10, 5186-5190.
Eckberg et al., "Diversity of the Human Intestinal Microbial Flora" Science, 308, 1635 (2005).
Edgar, "Search and clustering orders of magnitude faster than BLAST", Bioinformatics, 2010, 26:19, 2460.
Finegold et al., "Pyrosequencing study of fecal microflora of autistic and control children", Anaerobe 2010, 16 444.
Finegold et al., Gastrointestinal Microflora Studies in Late-Onset Autism Clinical Infectious Diseases, 2002, 35, S6.
Garcia-Pena et al., "Anaerobic digestion and co-digestion processes of vegetable and fruit residues: Process and microbial ecology", Bioresource Technology, 2011, 102, 9447.
Lee et al., "Prioritizing candidate disease genes by network-based boosting of genome-wide association data" Genome Research, 2011, 21:1, 1109-1121.
Lee et al., "Discriminative prediction of mammalian enhancers from DNA sequence", 2011 Genome Research, 21, 2167-2180.
Gill et al., "Metagenomic Analysis of the Human Distal Gut Microbiome" Science, 2006, 312, 1355-1359.
Goehler et al., "Campylobacter jejuni infection increases anxiety-like behavior in the holeboard: possible anatomical substrates for viscerosensory modulation of exploratory behavior", Brain Behavior Immunology, 2008, 22:3, 354.
Hanley & McNeil, "The Meaning and Use of the Area under a Receiver Operting Characteristic Cuve", Radiology, 1982, 143, 29.
Hayashi et al., "*Prevotella copri* sp. nov. and Prevotella stercorea sp. nov., isolated from human faeces" 57 International Journal of Systematic and Evolutionary Microbiology, 2007, 941-946.
Holst et al., "Biochemistry and cell biology of bacterial endotoxins" FEMS Immunology and Medical Microbiology, 1996, 16, 83.
Horvath et al., "Gasrointestinal abnormalities in children with autistic disorder" Journal of Pediatrics, 1999, 135:5, 559.
Huws et al., "As yet uncultured bacteria phylogenetically classified as Prevotella, Lachnospiraceae incertae sedis and unclassified Bacteroidales, Clostridiales and Ruminococcaceae may play a predominant role in ruminal biohydrogenationemion" Environmental Microbiology, 2011, 13, 1500.
Ivanov et al., "Induction of intestinal Th17 cells by segmented filamentous bacteria" Cell, 2009, 139:3, 485.
James et al., "Metabolic biomarkers of increased oxidative stress and impaired methylation capacity in children with autism" Journal of Clinical Nutrition, 2004, 80, 1611.
Jia et al., "Gut mictrobiota: a potential new territory for drug targeting" Nature Reviews-Drug Discovery, 2008, 7, 123.
Kaper et al., "Pathogenic *Escherichia coli*" Nature Reviews—Microbiology, 2004, 2, 123.
Kitajka et al., Effects of dietary omega-3 polyunsaturated fatty acids on brain gene expression, PNAS, 2004, 101:30 10931.
Kostic et al., "Genomic analysis identifies association of Fusobacterium with colorectal carcinoma" Genome Research, 2011, 22, 292-298.
Kushak et al., "Intestinal disaccharidase activity in patients with autism" Autism, 2011, 15:3, 285.

Kyselova et el., Alterations in the Serum Glycome Due to Metastatic Prostate Cancer, Journal of Proteome Research, 2007, 6, 1822-1832.
Lederberg, "Infectious History", Science, 2000, 288, 287.
Lee & Mazmanian, "Has the Microbiota Played a critical Role in the Evolution of the Adaptive Immune System?", 2010, 330, 1766.
Lonsdale et al., "Treatment of autism spectrum children with thiamine tetrahydroturfuryl disulfide: A pilot study", Neuroendocrinology Letters, 2002, 23, 303.
MacFabe et al., "Short-chain fatty acid fermentation products of the gut microbiome: implications in autism spectrum disorders", Behavior Brain Research, 2011, 217, 47.
Meadows, "Gut Bacteria May OVerride Genetic Protections againast Diabetes", PLOS Biology, 2011, 9:12, e1001215.
Minami et al., "Roles of nitric oxide and prostaglandins in the increased permeability of the blood-brain barrier caused by lipopolysaccharide" Environmental Toxicology and Pharmacology, 1998, 5, 35-41.
Minami et al., "Effects of lipopolysaccharide and chelator on mercury content in the cerebrum of thimerosal administered mice", Environmental Toxicology and Pharmacology, 2007, 24, 316.
Molloy & Manning-Courtney, "Prevalence of chronic gastrointestinal symptoms in children with autism and autistic spectrum disorders" Autism, 2003, 7:2, 165-171.
Mulloy et al., "Gluten-free and casein-free diets in the treatment of autism spectrum disorders: A systematic review" Researhc in Autism Spectrum Disorders, 2010, 4, 328.
Niehus & Lord, "Early Medical History of Children with Autism Spectrum Disorders" Journal of Developmental and Behavioral Pediatrics, 2006, 27:2, S120.
Cole et al., "The Ribosomal Database Project (RDP-II): previewing a new autoaligner that allows regular updates and the new prokaryotic taxonomy" Nucleic Acids Research, 2003, 31:1, 442-443.
O'Hara et al., "Functional modulation of human intestinal epithelial cell responses by Bifidobacterium infantis and Lactobacillus salivarius" Immunology, 2006, 118, 202.
Ochoa-Reparaz et al., "Gut, Bugs, and Brain: Role of Commensal Bacteria in the Control of Central Nervous System Disease", Annals Neurology, 2011, 69, 240-247.
Parracho et al., "Differences between the gut microflora of children with autistic spectrum disorders and that of healthy children" Journal of Medical Microbiology, 2005, 54, 987.
Qin et al., "A human gut microbial gene catalogue established by metagenomic sequencing" Nature, 2010, 464, 59.
Robertson et al., "Intestinal Permeability and Glucagon-like peptide-2 in Children with Autism: A Controlled Pilot Study", Journal of Autism Development Disorder, 2008, 38, 1066.
Robinson et al., "Characterization of the Cecal Bacteria of Normal Pigs", Applied and Environmental Microbiology, 1981, 41, 950.
Round et al., "The Toll-like receptor pathway establishes commensal gut colonization", Science, 2011, 332, 974-977.
Salazar et al., "Exopolysaccharides Produced by Intestinal Bifidobacterium Strains Act as Fermentable Substrates for Human Intestinal Bacteria", Applied Environmental Microbiology, 2008, 74, 4737.
Sandler et al., "Short-Term Benefit From Oral Vancomycin Treatment of Regressive-Onset Autism", Journal of Child Neurology, 2000, 15, 429.
Schauer & Falkow, "Attaching and Effacing Locus of a Citrobacterfreundii Biotype That Causes Transmissible Murine Colonic Hyperplasia" Infectious Immunology, 1993, 61:6, 2486.
Schloss et al., "Introducing mothur: Open-Source, Platform-Independent, Community-Supported Software for Describing and Comparing Microbial Communities", Applied and Environmental Microbiology , 2009, 75, 7537.
Schneider et al., "Oral Human Immunoglobulin for Children with Autism and Gastrointestinal Dysfunction: A Prospective, Open-Label Study" Journal of Autism Development Disorder, 2006, 36, 1053.
Song et al., "Real-Time PCR Quantitation of Clostridia in Feces of Autistic Children" Applied and Environmental Microbiology, 2004, 70:11, 6459.

(56) References Cited

OTHER PUBLICATIONS

Sun et al., "Tag-Encoded FLX Amplicon Pyrosequencing for the Elucidation of Microbial and Functional Gene Diversity in Any Environment" Methods and Applications, Methods in Molecular Biology, 2011, 733, 129.
Tap et al., "Towards the human intestinal microbiota phylogenetic core" Environmental Microbiology, 2009, 11:10, 2574.
Trent et al.,"Diversity of endotoxin and its impact on pathogenesis" Journal Endotoxin Research, 2006, vol. 12, p. 205.
Turnbaugh et al., "A core gut microbiome in obese and lean twins" Nature, 2009, 457, 480-484.
Udall et al., "Development of Gastrointestinal Mucosal Barrier. I. The Effect of Age on Intestinal Permeability to Macromolecules", Journal of Pediatric Research, 1981, 15:241-244.
Passel et al., "The Genome of Akkermansia muciniphila, a Dedicated Intestinal Mucin Degrader, and Its Use in Exploring Intestinal Metagenomesvan", 2011, 6 Plos One.
Vidhyalakshmi et al.,"Encapsulation "The Future of Probiotics"-A Revew" 2009Advances in Biological Research, 3, 96.
Wang et al., "Low Relative Abundances of the Mucolytic Bacterium Akkermansia muciniphila and *Bifidobacterium* spp. in Feces of Children with Autism" Applied Environmental Microbiology, 2011, 77, 6718.
Warnock & Peck, "A roadmap for biomarker qualification" Nature, 2010, 28, 444.

Williams et al., "Impaired Carbohydrate Digestion and Transport and Mucosal Dysbiosis in the Intestines of Children with Autism and Gastrointestinal Disturbances" Plos One, 2011, 6.
Willing et al., "Shifting the balance: antibiotic effects on host—microbiota mutualism" Nature Review of Microbiology, 2011, 9, 233.
Wolcott et al.,"Evaluation of the bacterial diversity among and within individual venous leg ulcers using bacterial tag-encoded FLX and Titanium amplicon pyrosequencing and metagenomic approaches" Bmc Microbiology, 2009, 9.
Wu et al., "Focused Evolution of HIV-1 Neutralizing Antibodies Revealed by Structures and Deep Sequencing" Science, 2011, 333, 105.
Zhang et al., "Human gut microbiota in obesity and after gastric bypass" PNAS, 2009, 106, 2365.
Zhu et al., "Altered giutathione homeostasis in animals prenatally exposed to lipopolysaccharide" Neurochemistry International, 2007, 50, 671.
Gondalia et al., "Faecal rnicrobiota of individuals with autism spectrum disorder", Electronic Journal of Applied Psychology, vol. d, No. 2, pp. 24-29 (2010).
International Search Report, PCT/US2013/032668, date of mailing Jul. 5, 2013, 4 pages.
International Written Opinion, PCT/US2013/032668, date of mailing Jul. 5, 2013, 7 pages.

* cited by examiner

MICROBIOME MARKERS AND THERAPIES FOR AUTISM SPECTRUM DISORDERS

CROSS REFERENCE TO RELATED APPLICATIONS

This application is a U.S. national stage of International Application No. PCT/US2013/032668, filed Mar. 15, 2013, which claims the benefit of U.S. Provisional Patent Application 61/651,846, filed on May 25, 2012, each of which is hereby incorporated by reference in its entirety.

FIELD OF THE INVENTION

The present invention relates to microbiology, neurology, and nutritional physiology.

BACKGROUND OF THE INVENTION

The human gut hosts millions of bacteria, which harmoniously balance the immune system, help digest food, produce vitamins, and promote gastrointestinal (GI) motility. Loss of homeostasis in the gut may contribute to an imbalance associated with disease states, such as immune and neurological disorders, and cause GI problems, which can exacerbate other disorders or symptoms. For example, Autism Spectrum Disorders (ASDs) are complex neurobiological disorders whose chief manifestations are qualitative impairment in social interaction and communication and restricted repetitive and stereotyped patterns of behavior, interests, and activities. There has been a world-wide increase in the diagnosis of ASD, which has reached epidemic level. ASD subjects and their families face difficulties in treatment because ASD does not share a common etiology. Both genetic and environmental factors are important in the etiology of autism, with a recent large twin concordance study suggesting that environmental factors are at least as important, if not more important, than genetic ones. A potentially important environmental factor is abnormal intestinal flora that often interacts with other factors such as intestinal permeability and transport of toxic substances. Hence, there remains a need for understanding the role of the microbiome in the healthy gut versus the unhealthy gut, and, in particular in the context of ASD subjects.

SUMMARY OF THE INVENTION

In at least one aspect, an assay includes subjecting nucleic acid extracted from a test sample of a human subject to a genotyping assay that detects at least one of *Prevotella, Coprococcus*, Prevotellaceae, or Veillonellaceae bacteria, the test sample including microbiota from a gut of the subject; determining a relative abundance of the at least one of *Prevotella, Coprococcus*, Prevotellaceae, or Veillonellaceae bacteria that is below a predetermined abundance; and selecting, when the relative abundance is below the predetermined abundance, a treatment regimen that comprises at least one of modifying microbiota of the gut of the subject using at least one of a prebiotic, probiotic, or pharmaceutical, or applying a therapeutic regimen for treating autism spectrum disorders.

In at least one aspect, an assay includes subjecting protein extracted from a test sample of a human subject to a protein assay that determines at least one protein indicative of at least one of *Prevotella, Coprococcus*, Prevotellaceae, or Veillonellaceae bacteria, the test sample including microbiota from a gut of the subject, determining a relative abundance of the at least one of *Prevotella, Coprococcus*, Prevotellaceae, or Veillonellaceae bacteria that is below a predetermined abundance, and selecting, when the relative abundance is below the predetermined abundance, a treatment regimen that comprises at least one of modifying microbiota of a gastrointestinal tract of the subject, or applying a therapeutic regimen for treating autism spectrum disorders.

In at least one aspect, a method of selecting a treatment regimen for a human subject, includes subjecting a test sample from the human subject, including microbiota from a gut of the subject, to at least one of nucleic acid extraction, or protein extraction; detecting, using at least one of the extracted nucleic acid or protein, a relative abundance of at least one of *Prevotella, Coprococcus*, Prevotellaceae, or Veillonellaceae bacteria in the gut of the subject; comparing the detected relative abundance of the at least one of *Prevotella, Coprococcus*, Prevotellaceae, or Veillonellaceae bacteria to a predetermined abundance of the at least one of *Prevotella, Coprococcus*, Prevotellaceae, or Veillonellaceae bacteria; and selecting, when the relative abundance is below the predetermined abundance, the treatment regimen comprising at least one of modifying microbiota of a gastrointestinal tract of the subject, or applying a therapeutic regimen for treating autism spectrum disorders.

In at least one aspect, a method of increasing balance of a microbiome of a gut of a human subject having autism spectrum disorder (ASD) includes determining a relative abundance of at least one of *Prevotella, Coprococcus*, Prevotellaceae, or Veillonellaceae bacteria in the gut of the subject; and administering, when the relative abundance is below a predetermined amount, at least one of a prebiotic, probiotic, or pharmaceutical capable of modifying the relative abundance of the at least one of *Prevotella, Coprococcus*, Prevotellaceae, or Veillonellaceae bacteria in the gut.

In at least one aspect, a method of treating a human subject with autism spectrum disorder gut-related symptoms, includes administering, to the subject, a prebiotic to stimulate growth of at least one of *Prevotella, Coprococcus*, Prevotellaceae, or Veillonellaceae bacteria in a gut of the subject, wherein a relative abundance of the at least one of *Prevotella, Coprococcus*, Prevotellaceae, or Veillonellaceae bacteria in the gut of the subject is below a predetermined abundance.

In at least one aspect, a method of selecting a human subject with autism spectrum disorders (ASD) or gut-related symptoms for inclusion in or exclusion from a clinical trial, comprising subjecting a test sample from a human subject, including microbiota from a gut of the subject, to at least one of nucleic acid extraction, or protein extraction; detecting, using at least one of the extracted nucleic acid or protein, a relative abundance of at least one of *Prevotella, Coprococcus*, Prevotellaceae, or Veillonellaceae bacteria in the gut of the subject; and selecting the subject for inclusion in the clinical trial when the relative abundance of the at least one of *Prevotella, Coprococcus*, Prevotellaceae, or Veillonellaceae bacteria is below a first predetermined abundance, the first predetermined abundance being an upper-limit for indicating at least one of ASD or gut-related symptoms, and selecting the subject for exclusion from the clinical trial when the relative abundance is above a second predetermined abundance, the second predetermined abundance being a lower limit for indicating at least one of a neurotypical subject or no gut-related symptoms.

In at least one aspect, a computer system for detecting the relative abundance of *Prevotella, Coprococcus*, Prevotellaceae, or Veillonellaceae bacteria includes one or more display devices; one or more processors; and at least one memory device storing instructions that, when executed by at least one of the one or more processors, cause the computer system to: subject, via at least one assay module, at least one of: nucleic acid extracted from a test sample of a human subject to a genotyping assay that determines a genus-level genotype of the extracted nucleic acid, the test sample including microbiota from a gut of the subject, or protein extracted from a test sample of a human subject to a protein assay that determines at least one protein indicative of at least one of *Prevotella, Coprococcus*, Prevotellaceae, or Veillonellaceae bacteria, the test sample including microbiota from a gut of the subject; and determine, via at least one determination module, a relative abundance of the at least one of *Prevotella, Coprococcus*, Prevotellaceae, or Veillonellaceae bacteria that is below a predetermined abundance; display, via at least one of the one or more display devices, at least one determined relative abundance.

In at least one aspect, a computer system for selecting a treatment regimen for a patient includes one or more display devices, one or more processors, and at least one memory device storing instructions that, when executed by at least one of the one or more processors, cause the computer system to: subject, via at least one testing module, a test sample from the human subject, including microbiota from a gut of the subject, to at least one of nucleic acid extraction or protein extraction; detect, via at least one detecting module, at least one of the extracted nucleic acid or protein, a relative abundance of at least one of *Prevotella, Coprococcus*, Prevotellaceae, or Veillonellaceae bacteria in the gut of the subject; and compare, via at least one comparing module, the detected relative abundance of the at least one of *Prevotella, Coprococcus*, Prevotellaceae, or Veillonellaceae bacteria to a predetermined abundance of the at least one of *Prevotella, Coprococcus*, Prevotellaceae, or Veillonellaceae bacteria; select, when the relative abundance is decreased, the treatment regimen comprising at least one of: modifying microbiota of a gastrointestinal tract of the subject, or applying a therapeutic regimen for treating autism spectrum disorders.

DETAILED DESCRIPTION OF PREFERRED EMBODIMENTS

Figure 1A:
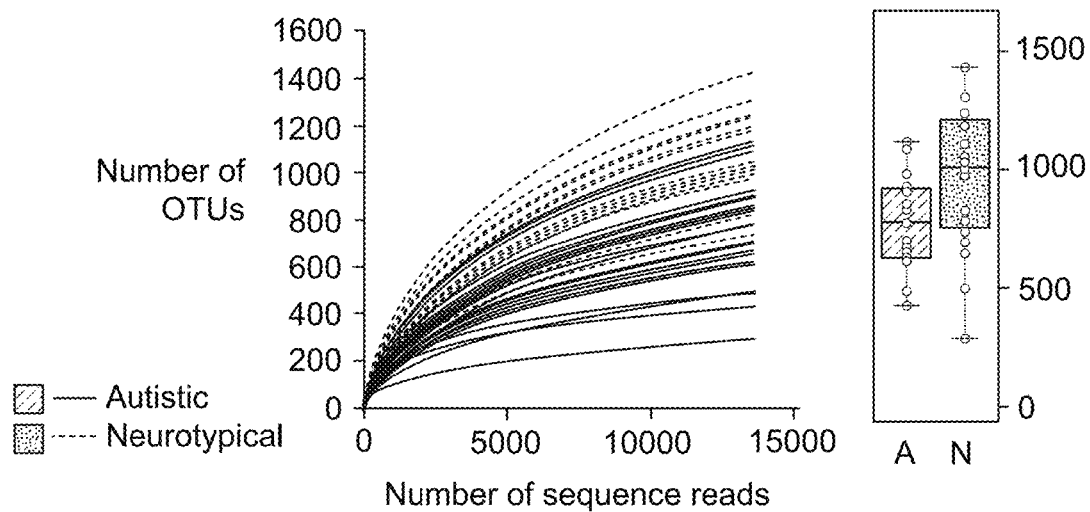
FIG. 1A illustrates rarefaction curves showing unique operating taxonomic units (OTUs) at the 95% threshold, as well as a box graph at the rarefied sequence number for autistic (A) and neurotypical (N) subjects.

It should be understood that this invention is not limited to the particular methodology, protocols, reagents, etc., described herein and, as such, may vary. The terminology used herein is for the purpose of describing particular embodiments only and is not intended to limit the scope of the present invention, which is defined solely by the claims. Unless defined otherwise, all technical and scientific terms used herein have the same meaning as those commonly understood to one of ordinary skill in the art to which this invention pertains.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

All patents and other publications identified are expressly incorporated by reference herein for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The human intestine hosts up to $10^{14}$ bacteria, which harmoniously balance the immune system, help digest food, produce vitamins, and promote GI motility. Hence, loss of homeostasis in the gut may contribute to the imbalance of disease states, such as ASD-associated immune and neurological systems, and cause GI problems, which can exacerbate autistic symptoms. The present embodiments provide for the characterization of the healthy gut microbiome and for the characterization of the gut microbiome in Autism spectrum disorders (ASD) subjects. ASDs are complex neurobiological disorders. ASD-diagnosed children have increased noticeably, and ASD has entered into world-wide epidemic level. Both genetic and environmental factors are important in the etiology of autism, but one potentially important environmental factor that has not been deeply explored is abnormal intestinal flora, which often interacts with other factors such as intestinal permeability and transport of toxic substances. Many autistic children and adults suffer from gastrointestinal (GI) problems, and it is likely that abnormal intestinal flora may contribute to those problems. Considering the interactions of intestinal microflora and the central nervous system, human intestinal microbes might also contribute to the autistic symptoms regardless of the manifestation as GI problems.

Techniques for characterizing the microbiome include use of nucleic acid and/or proteins. Nucleic acid analysis includes analysis of, for example, DNA, RNA, mRNA, rRNA, and/or tRNA, and can be accomplished using, for example, pyrosequencing, qPCR, RT-qPCR, clone libraries, DGGE, T-RFLP, ARISA, microarrays, FIFH, dot-blot hybridization, next generation sequencing, and any other DNA hybridization methods that will detect a specific sequence. Protein analysis includes, for example, 2-Dimensional Gel Electrophoresis, 2-Dimensional Difference Gel Electrophoresis (2D-DIGE), MALDI TOF-MS, (2D-) LC-ESI-MS/MS, AQUA, and iTRAQ. These characterizations can be combined with rigorous statistical analysis to determine the constituents of the microbiome. In one non-limiting example, parallel pyrosequencing, provides for high-capacity, low-cost sequencing. The present disclosure uses different statistical tests and the use of rigorous correction methods for multiple testing that strengthen the interpretation of the present data. Bioinformatics provides for the efficient definition of the characteristics and distributions of intestinal microflora between subjects.

A strong positive correlation exists between GI problems and ASD severity ($r=0.6$, $p<0.001$). Human intestinal microbes might also contribute to autistic symptoms because of the interactions of intestinal microbes and the central nervous system. Autistic children use oral antibiotics at an increased rate compared to neurotypical children, and increased use of antibiotics may eliminate beneficial bacteria and help pathogenic bacteria colonize the intestinal walls.

Many gram-negative bacteria work as pathogens because their cell wall contains lipopolysaccharide (LPS), which stimulates host immune systems to cause fever and neurological dysfunction. LPS can increase the permeability of the blood-brain barrier and increase mercury levels in the cerebrum, which may aggravate ASD. LPS also tends to decrease levels of glutathione, an important antioxidant involved in heavy metal detoxification. Lower levels of glutathione may increase the vulnerability of children to ASD and other neurologic disorders such as Parkinson's and Alzheimer's diseases. Pyrosequencing analysis revealed that *Desulfovibrio* and *Bacteroides vulgatus*, two bacterial species that have LPS in their cell walls, were detected at higher levels in autistic children than in neurotypical children. The gram-positive *Clostridium* is also of interest in the context of ASD because it may have an opportunistic role as endotoxin producer. *Clostridium boltae, C. histolyticum*, and subgroups I and XI also tend to be more abundant in autistic children than in neurotypical children. Enterotoxins from the *Clostridium* species may damage intestinal tissues, which may result in diarrhea and/or may increase absorption of large molecules such as casein and gluten. *Clostridium* species may also produce propionate, which may worsen ASD-like behavior in rat experiments. Additionally, oral vancomycin, an antibiotic that is generally effective against gram-positive bacteria including *Clostridium*, resulted in substantial temporary improvements in gastrointestinal and autistic symptoms in children with late-onset autism.

The human intestine also embraces numerous protective commensal microbes. Microbes domesticate the host and tend to survive together in the long run. *Bifidobacterium* and *Lactobacillus* are good examples of beneficial bacteria in the human intestine, and are often used as probiotics to promote motility. It has been observed that *Bifidobacterium* were less abundant in autistic children, but *Lactobacillus* were more abundant. Many *Clostridium* species are pathogenic, but it has been reported that the sub-group of *Clostridium* IV/XIVa have a beneficial role in maintaining a balanced immune system, similar to the segmented filamentous bacteria.

Molecular techniques such as those based on parallel sequencing enable thorough and systematic identification of intestinal microorganisms. From this, alterations in gut microbe composition can be linked to various human disorders. Despite the linkage between ASD and GI problems, however, no autism-related gut microbe composition profiles and their potential associations to disorder progress and diagnosis were previously observed. Therefore, a pilot study with neurotypical and autistic children was designed, as described herein, accompanied by comprehensive surveys on their GI problems and autistic symptoms. The intestinal microflora of the children enrolled was characterized using 454 GS FLX Titanium pyrosequencing. In-depth analyses revealed that there were significant differences in microbial diversity as well as in composition between the groups. Notably, the differences were more pronounced between neurotypical and autistic children than between autistic children with and without GI problems. The present disclosure provides an association between ASD and/or gut-related problems and gut microflora, which can be potential targets for therapeutics or diagnosis of ASD.

Stool samples were collected from neurotypical and autistic subjects (n=20 each after gender balancing), with the mean (±SD) ages of 8.3 (±4.4) and 7.1 (±3.2) years, respectively, as shown in Table 13 (see Example 1). Among all subjects, there were five female subjects (three neurotypical and two autistic subjects). To estimate the severity of GI symptoms, six categories of GI problems were surveyed, and each subject was scored for the total GI symptom index (6-GSI). In general, the 6-GSI scores in the autistic group were relatively higher (4.6±2.2) than those of neurotypical group (0.5±0.8). Additionally, the severity of GI problems was compared with autism severity, but the 6-GST score did not have a significant correlation with the ADOS score (sum of communication and social score), r=0.35, ATEC (r=0.24), or PDD-BI (r=0.12). Autistic subjects were further divided into two roughly equal-sized groups based on their GI symptoms: autistic-GI$^+$ (6-GSI≥6, n=8) and autistic-GI$^-$ (6-GSI<6, n=12), with an arbitrary score cutoff.

Figure 1B:
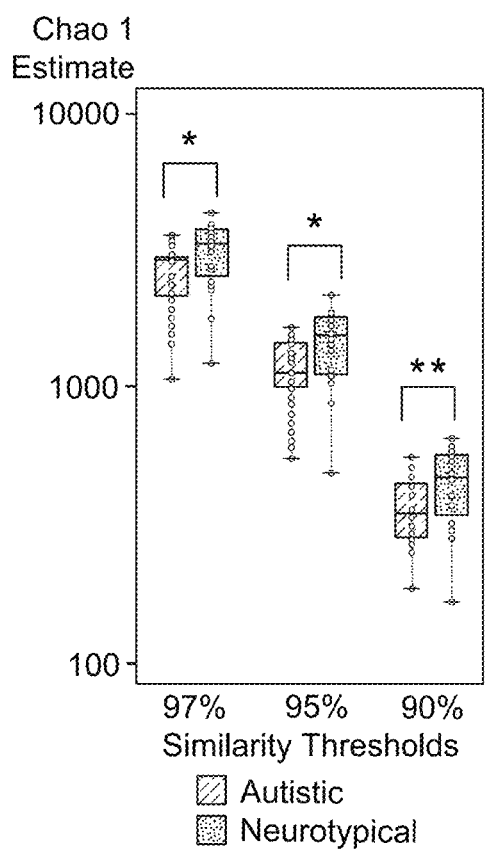
FIG. 1B illustrates Chao1 estimators between neurotypical (right-side box for each similarity threshold) and autistic (left-side box for each similarity threshold) groups at different similarity thresholds (*: $P<0.05$, **: $P<0.01$ by one-tailed Mann-Whitney test).
Figure 5A:
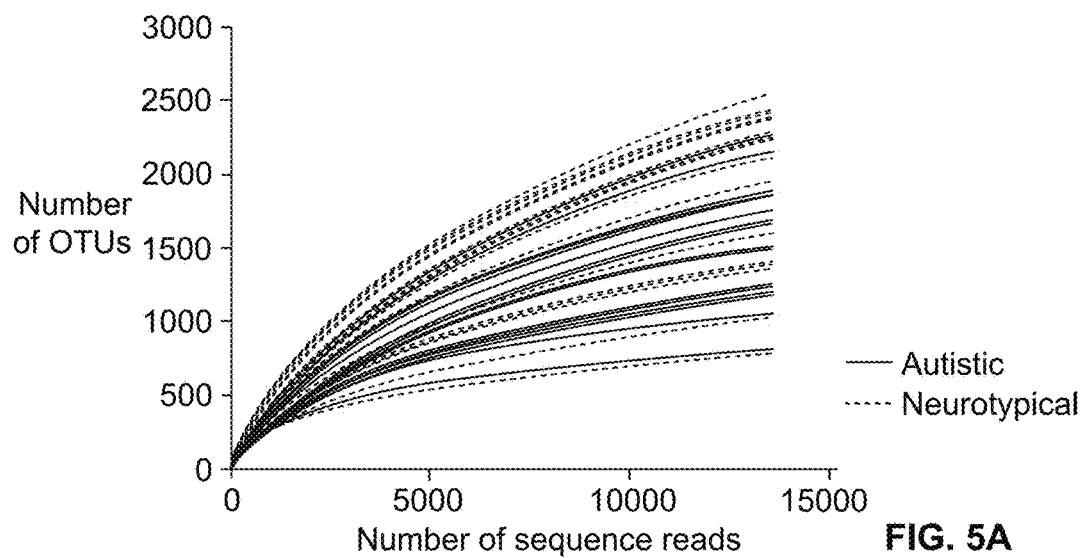
FIG. 5A presents rarefaction curves showing sequencing numbers and OTUs obtained by the UCLUST algorithm with a 97% sequence similarity threshold.
Figure 5B:
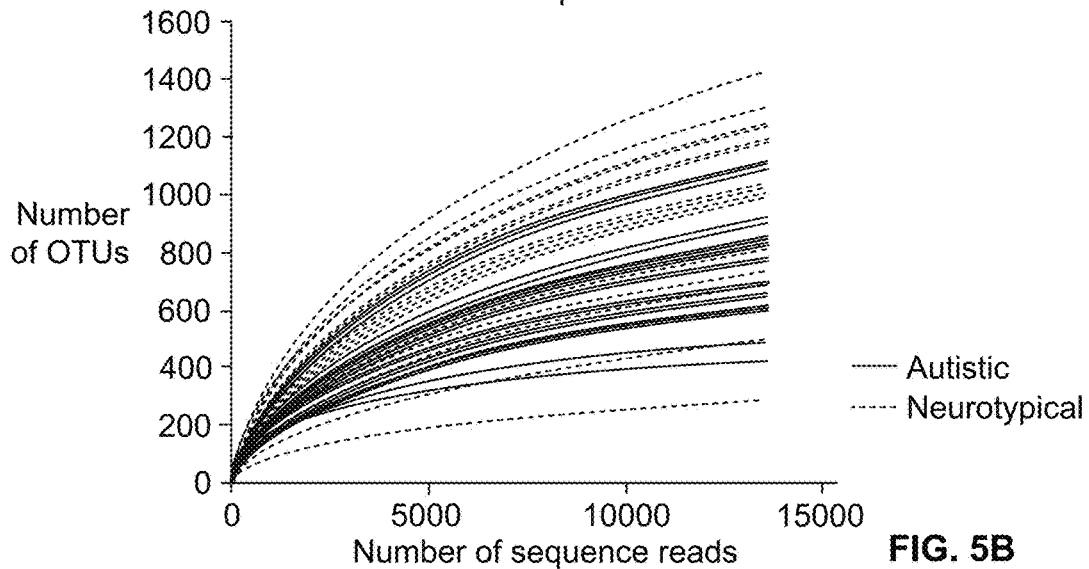
FIG. 5B presents rarefaction curves showing sequencing numbers and OTUs obtained by the UCLUST algorithm with a 95% sequence similarity threshold.
Figure 5C:
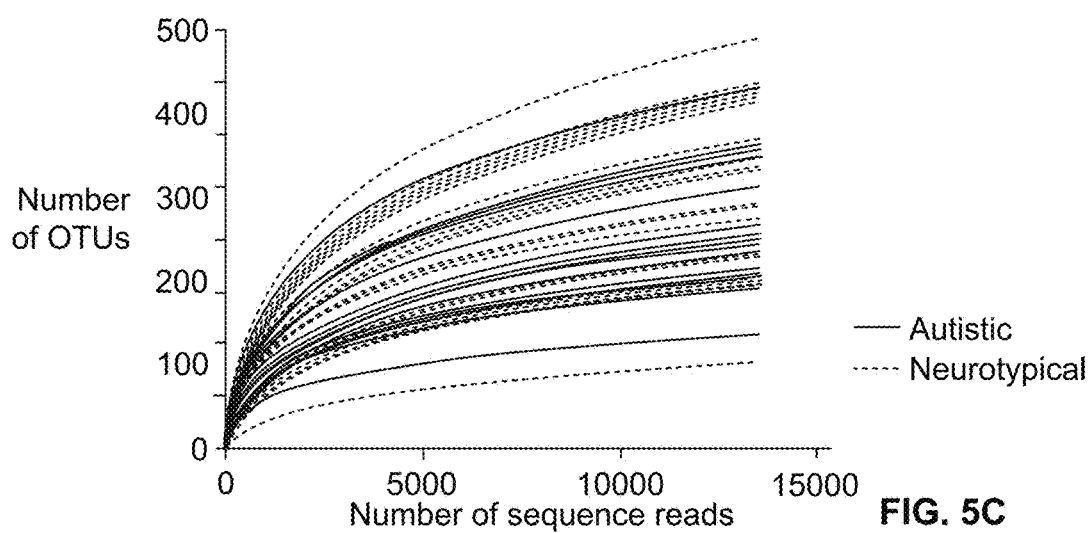
FIG. 5C presents rarefaction curves showing sequencing numbers and OTUs obtained by the UCLUST algorithm with a 90% sequence similarity threshold.

Autism-associated changes in intestinal microbial diversity were characterized. Maintaining sufficient bacterial richness and diversity is important for providing gut microbiota (alternatively, "microflora") with functional redundancy, adaptability, and, thus, systematic robustness against environmental changes. Therefore, with the sequences of 16S rRNA genes, bacterial richness and diversity between groups were compared. An average of about 24,600 sequence-reads per child (about 985,500 sequences in total) was obtained after quality control, and the sequences were classified into OTUs based on their sequence similarities. Rarefaction curves at the 95% (FIG. 1A) and 97% (FIG. 5B) sequence similarity levels showed that neurotypical individuals had a higher number of observed bacterial species than autistic individuals. As an alternative method to estimate the richness and diversity, the nonparametric Chao1 estimator was employed. Similar to the rarefaction data, the neurotypical group had a significantly higher number of estimated OTUs at the 90%, 95%, and 97% thresholds (see FIG. 1B and Table 1), which indicates that the neurotypical group had higher bacterial richness and diversity than the autistic group.

TABLE 1

Microbial diversity indices with OTUs obtained by UCLUST Chao1 estimator

| UCLUST threshold | 90% | 95% | 97% |
| --- | --- | --- | --- |
| Neurotypical | 451 | 1453 | 3088 |
| Autistic | 364 | 1165 | 2533 |
| P values (Student's t-test/ Mann-Whitney test) | 0.013/0.010 | 0.010/0.008 | 0.014/0.008 |

TABLE 2

Microbial diversity indices with OTUs obtained by UCLUST Shannon diversity index (H)

| UCLUST threshold | 90% | 95% | 97% |
| --- | --- | --- | --- |
| Neurotypical | 3.32 | 4.57 | 5.63 |
| Autistic | 3.27 | 4.43 | 5.38 |
| P values (Student's t-test/ Mann-Whitney test) | 0.42/0.10 | 0.295/0.12 | 0.12/0.08 |

TABLE 3

Microbial diversity indices with OTUs obtained by UCLUST Shannon evenness index (E)

| UCLUST threshold | 90% | 95% | 97% |
| --- | --- | --- | --- |
| Neurotypical | 0.57 | 0.66 | 0.74 |
| Autistic | 0.58 | 0.66 | 0.73 |
| P values (Student's t-test/ Mann-Whitney test) | 0.35/0.38 | 0.46/0.21 | 0.25/0.14 |

TABLE 4

Microbial diversity indices with OTUs obtained by UCLUST Phylogenetic Diversity (PD)

| UCLUST threshold | 90% | 95% | 97% |
| --- | --- | --- | --- |
| Neurotypical | 29.4 | 59.7 | 71.5 |
| Autistic | 24.9 | 51.2 | 62.8 |
| P values (Student's t-test/ Mann-Whitney test) | 0.018/0.021 | 0.039/0.021 | 0.062/0.031 |

Figure 1C:
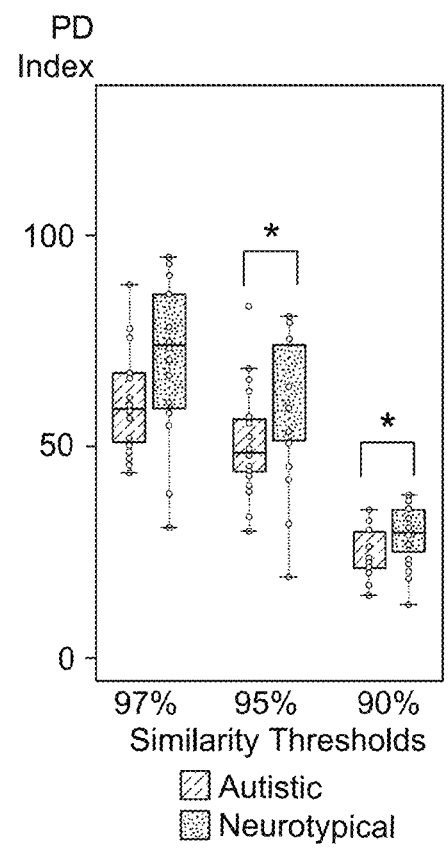
FIG. 1C illustrates the phylogenetic diversity (PD) index between neurotypical (right-side box for each similarity threshold) and autistic (left-side box for each similarity threshold) groups at different similarity thresholds (*: $P<0.05$, **: $P<0.01$ by one-tailed Mann-Whitney test).

Another estimator of microbial diversity, the Shannon diversity index (H), showed similar trends but without statistical significance, and the Shannon evenness index (E) was comparable among groups (see Tables 2, 3). However, the Phylogenetic Diversity (PD) revealed that the neurotypical group harbored more diverse gut microbiota than the autistic group did (P<0.05 by one-tailed Mann-Whitney test, as shown in FIG. 1C and Table 4). In addition, the correlation between bacterial richness/diversity and the severity of GI problems within the autistic group was evaluated, and bacterial richness was negatively correlated with GI severity (see Table 5). Taken together, these data suggest that the presence of autistic symptoms, but not necessarily the severity of GI problems, is strongly associated with reduced richness and diversity of gut microflora, which may result in a decrease in microbial redundancy and, as a result, may alter physiological functionality and robustness in children with ASD.

TABLE 5

Correlation between microbial richness/diversity and severity of GI problems within the autistic group. (P1 and P2: p values from Fisher transformation and permutation test).

| UCLUST threshold | | 90% | 95% | 97% |
| --- | --- | --- | --- | --- |
| (A) Chao1 estimator | | | | |
| Pearson | r value | −0.337 | −0.416 | −0.416 |
| | $P_1/P_2$ | 0.158/0.079 | 0.076/0.039 | 0.077/0.038 |
| Spearman rank | r value | −0.267 | −0.378 | −0.395 |
| | $P_1/P_2$ | 0.269/0.133 | 0.111/0.054 | 0.095/0.047 |
| (B) Shannon diversity index | | | | |
| Pearson | r value | −0.21 | −0.125 | 0.013 |
| | P1/P2 | 0.388/0.193 | 0.609/0.303 | 0.957/0.522 |
| Spearman rank | r value | −0.28 | −0.141 | −0.058 |
| | P1/P2 | 0.245/0.121 | 0.565/0.278 | 0.815/0.406 |
| (C) Shannon evenness index | | | | |
| Pearson | r value | −0.147 | 0.015 | 0.161 |
| | P1/P2 | 0.549/0.274 | 0.952/0.524 | 0.509/0.744 |
| Spearman rank | r value | −0.204 | −0.049 | 0.064 |
| | P1/P2 | 0.402/0.202 | 0.843/0.42 | 0.795/0.6 |

TABLE 5-continued

Correlation between microbial richness/diversity and severity
of GI problems within the autistic group. (P1 and P2: p values
from Fisher transformation and permutation test).

| UCLUST threshold | | 90% | 95% | 97% |
|---|---|---|---|---|
| (D) Phylogenetic Diversity (PD) | | | | |
| Pearson | r value | 0.154 | 0.059 | 0.093 |
| | $P_1/P_2$ | 0.528/0.738 | 0.811/0.592 | 0.705/0.640 |
| Spearman rank | r value | 0.178 | 0.003 | 0.028 |
| | $P_1/P_2$ | 0.465/0.771 | 0.991/0.504 | 0.908/0.544 |

One autistic sample with significantly fewer sequences (about 8,800 reads) than the average (about 25,000 reads) was excluded from further analyses.

Figure 6:
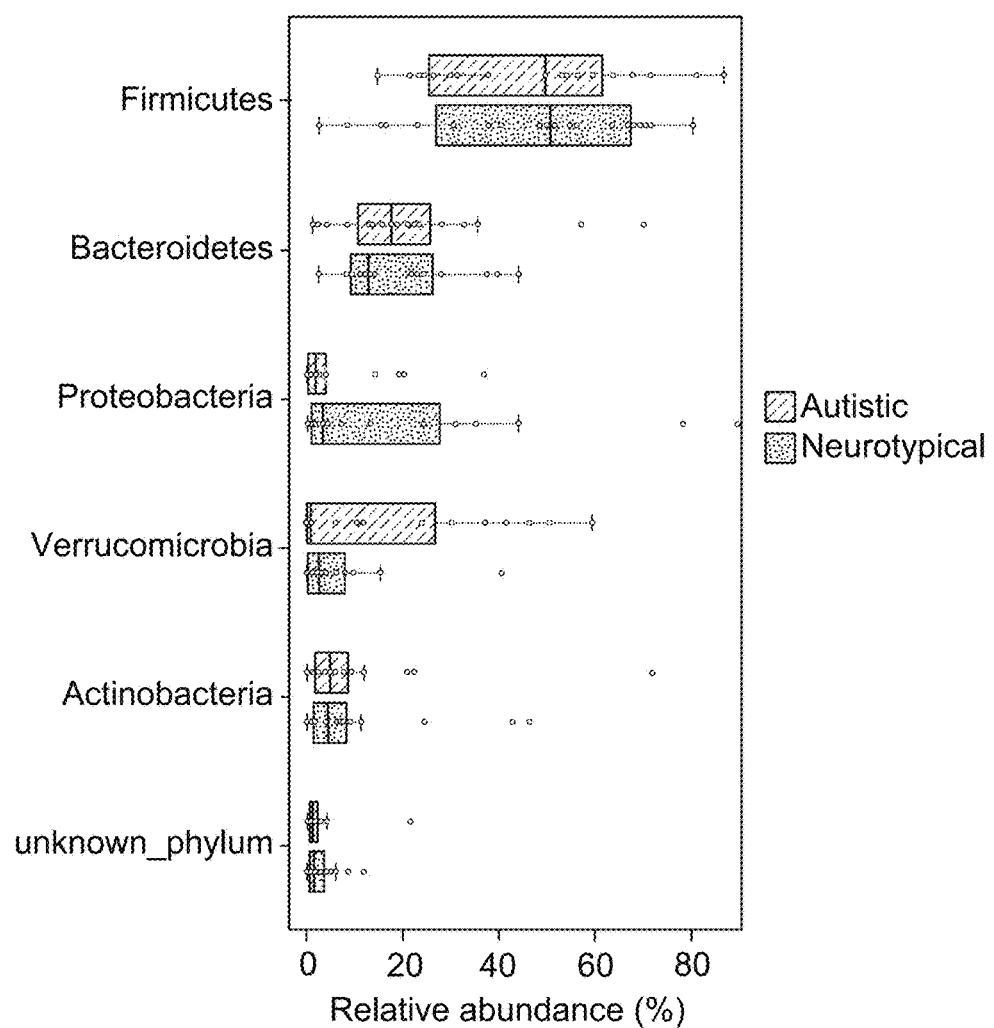
FIG. 6 shows the relative abundance of gut microbiome at the phylum level. The left-side boxes for each bacterium represent autistic children, and the right-side boxes for each bacterium represent neurotypical children.

Additionally, autism-associated changes in gut microflora at phylum level were characterized. For detailed taxonomic analyses, individual sequences were classified by the Ribosomal Database Project ("RDP") classifier described by Wang, Q, G. M. Garrity, J. M. Tiedje, and J. R. Cole, *Naïve Bayesian Classifier for Rapid Assignment of rRNA Sequences into the New Bacterial Taxonomy*, 73 APPL. ENVIRON MICROBIOL. 16:5261-7 (2007), which is hereby incorporated by reference in its entirety. The RDP classifier assigned approximately 97% of total sequences to fifteen known phyla. Firmicutes and Bacteroidetes were the two most dominant phyla, and the phyla Proteobacteria, Actinobacteria, and Verrucomicrobia were also relatively abundant (as shown in Table 6). These five phyla comprised an average of about 97.2% of total classifiable sequences across samples. Comparison of mean abundance between groups by the Student's t-test showed that the phyla Proteobacteria and Verrucomicrobia were more abundant in neurotypical and autistic groups, respectively, but this showed no statistical significance after correction for multiple testing (FIG. 6 and Table 6, P adjusted). Because the data were not normally distributed and contained many zero values, the non-parametric Mann-Whitney test was used as the main statistical test throughout this study. The tests showed that there was no significant difference in the relative abundance of individual phyla between the neurotypical and autistic groups (Table 6).

TABLE 6

Relative abundance of fifteen phyla detected in all subjects

| | Median % and 25/75 percentiles | | Student's t-test | | MW-test | |
|---|---|---|---|---|---|---|
| Phylum | Autism | Neurotypical | P | P adj. | P | P adj. |
| Firmicutes | 52.3 | 53.7 | 0.486 | 0.486 | 0.450 | 0.480 |
| | (30.3/62.3) | (31.8/68.7) | | | | |
| Bacteroidetes | 20.0 | 13.7 | 0.287 | 0.387 | 0.373 | 0.427 |
| | (11.8/24.6) | (10.6/25.3) | | | | |
| Actinobacteria | 4.72 | 4.07 | 0.450 | 0.480 | 0.483 | 0.483 |
| | (1.83/8.36) | (2.04/7.75) | | | | |
| Proteiobacteria | 2.08 | 3.45 | 0.049 | 0.248 | 0.063 | 0.263 |
| | (0.47/4.66) | (1.46/22.7) | | | | |
| Verrucomicrobia | 1.02 | 2.62 | 0.039 | 0.248 | 0.363 | 0.427 |
| | (0.09/26.2) | (0.30/7.46) | | | | |
| Unknown phylum | 0.75 | 1.87 | 0.370 | 0.422 | 0.134 | 0.263 |
| | (0.67/2.64) | (0.87/3.55) | | | | |
| Cyanobacteria | 0.01 | 0.01 | 0.299 | 0.387 | 0.181 | 0.263 |
| | (<0.01/0.04) | (<0.01/0.03) | | | | |
| TM7 | 0.01 | 0.01 | 0.314 | 0.387 | 0.370 | 0.427 |
| | (<0.01/0.02) | (<0.01/0.06) | | | | |
| Fusobacteria | <0.01 | <0.01 | 0.124 | 0.248 | 0.175 | 0.263 |
| | (<0.01/<0.01) | (0/<0.01) | | | | |
| Acidobacteria | <0.01 | <0.01 | 0.119 | 0.248 | 0.149 | 0.263 |
| | (0/<0.01) | (0/<0.01) | | | | |
| Bacteria_incertae_sedis | <0.01 | <0.01 | 0.156 | 0.269 | 0.165 | 0.263 |
| | (0/<0.01) | (0/<0.01) | | | | |
| Chloroflexi | 0 | <0.01 | 0.112 | 0.248 | 0.087 | 0.263 |
| | (0/0) | (<0.01/<0.01) | | | | |
| Tenericutes | 0 | <0.01 | 0.075 | 0.248 | 0.044 | 0.263 |
| | (0/0) | (0/<0.01) | | | | |
| Synergistetes | 0 | <0.01 | 0.069 | 0.248 | 0.044 | 0.263 |
| | (0/0) | (0/<0.01) | | | | |
| Thermotogae | 0 | <0.01 | 0.111 | 0.248 | 0.087 | 0.263 |
| | (0/0) | (0/<0.01) | | | | |
| *Nitrospira* | 0 | <0.01 | 0.168 | 0.269 | 0.178 | 0.263 |
| | (0/0) | (0/<0.01) | | | | |

Figure 2A:
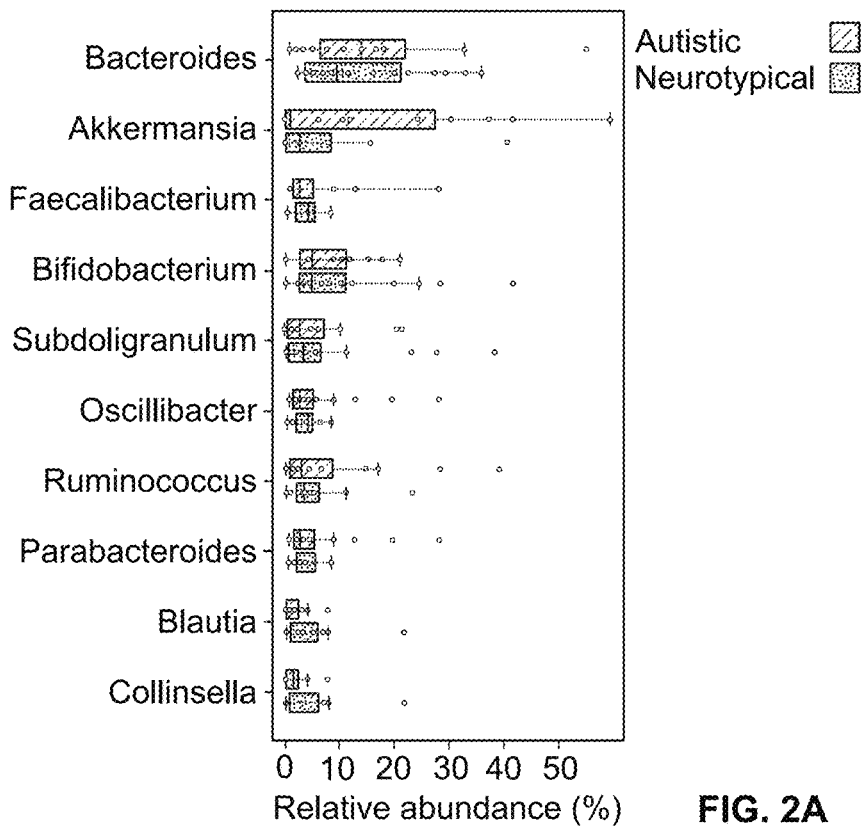
FIG. 2A shows the distribution of 39 subjects based on relative abundance of the top 10 most abundant genera for autistic (top box for each genera) and neurotypical (bottom box for each genera) subjects.

Further, autism-associated changes in gut microflora at the genus level were distinguished. Among 214 genera identified by the RDP classifier, the genera *Bacteroides, Faecalibacterium, Bifidobacterium, Akkermansia,* and *Subdoligranulum* were commonly the top five most abundant genera in both neurotypical and autistic groups, in which the five genera comprised about 38% and about 52% of total sequences, respectively (FIG. 2A and Table 7).

TABLE 7

Top 20 genera out of 214 known genera in neurotypical (N) and autistic (A) subjects.

| Normal | #N (n = 20) | % Total | Autistic | #A (n = 19) | % Total |
|---|---|---|---|---|---|
| *Bacteroides* | 20 | 13.11 | *Bacteroides* | 20 | 17.73 |
| *Faccalibacterium* | 20 | 9.20 | *Akkermansia* | 20 | 12.97 |
| *Bifidobacterium* | 20 | 5.89 | *Bifidobacterium* | 16 | 7.41 |
| *Akkermansia* | 19 | 5.22 | *Faecalibacterium* | 18 | 7.35 |
| *Subdoligranulum* | 20 | 4.64 | *Subdoligranulum* | 19 | 6.77 |
| *Oscillibacter* | 20 | 4.38 | *Blautia* | 18 | 3.56 |
| *Ruminococcus* | 19 | 1.88 | *Ruminococcus* | 20 | 2.85 |
| *Parabacteroides* | 20 | 1.82 | *Parabacteroides* | 20 | 2.48 |
| *Escherichic/Shigella* | 14 | 1.80 | *Oscillibacter* | 20 | 1.91 |
| *Collinsella* | 17 | 1.73 | *Parasutterella* | 13 | 1.29 |
| *Prevotella* | 15 | 1.40 | *Phascolarctobacterium* | 11 | 0.82 |
| *Anaerotruncus* | 19 | 1.21 | *Escherichic/Shigella* | 13 | 0.74 |
| *Phascolarctobacterium* | 7 | 1.16 | *Anaerotruncus* | 20 | 0.72 |
| *Blautia* | 20 | 1.12 | *Dialister* | 12 | 0.69 |
| *Paraprevotella* | 10 | 0.86 | *Butyricicoccus* | 16 | 0.67 |
| *Sutterella* | 13 | 0.70 | *Veillonella* | 16 | 0.67 |
| *Roseburia* | 20 | 0.53 | *Coprobacillus* | 18 | 0.67 |
| *Coprobacillus* | 20 | 0.52 | *Collinsella* | 14 | 0.62 |
| *Dialister* | 16 | 0.43 | *Alistipes* | 17 | 0.41 |
| *Citrobacter* | 13 | 0.41 | *Barnesiella* | 4 | 0.33 |

The subject numbers (#N and #A) are counts of subjects that contained corresponding genera in fecal samples. The average percentage of each genus is indicated in the column '% Total.'

Figure 7:
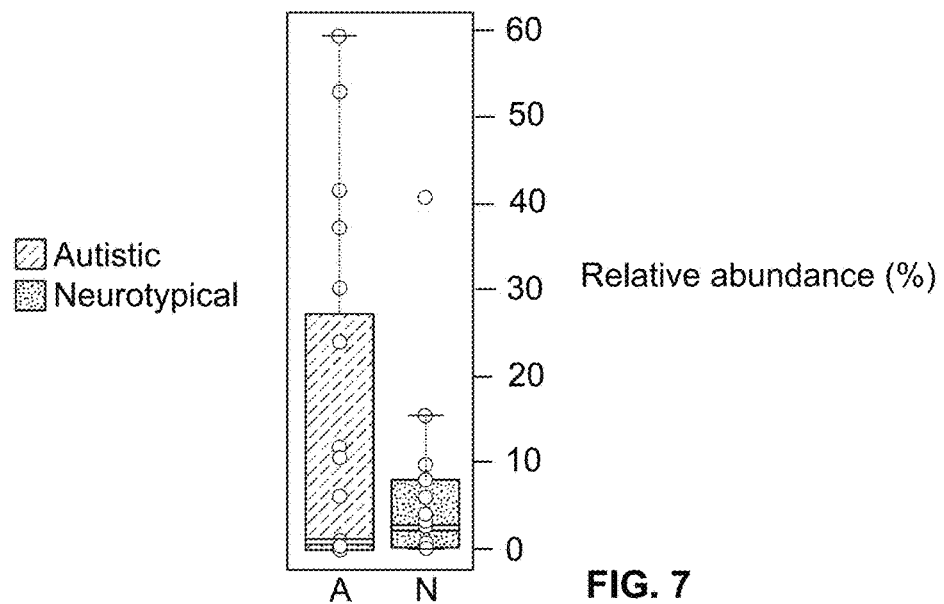
FIG. 7 illustrates the distribution of relative abundance of the genus *Akkermansia* in 39 subjects. N: neurotypical; A: autistic group.

Surprisingly, the *Akkermanisia* genus, a mucin degrader, was present at very high levels in several autistic and neurotypical subjects, representing about 30% to about 50% of all sequences (FIG. 7).

When the mean abundance of each genus was compared between groups by the unadjusted Student's t-test, the genera *Prevotella, Oscillibacter,* and *Paraprevotella* were more abundant in the neurotypical group, and the genus *Akkermansia* was more abundant in the autistic group (Table 8).

TABLE 8

Genera having significant difference, relative abundance.

(a) Neurotypical and autistic children (Adjusted P values were 0.245 for all listed genera)

| Family.Genus | P value | Median(25/75 percentiles) Neurotypical | Autism |
|---|---|---|---|
| Lachnospiraceae.*Coprococcus I* | 0.0333 | 0.04(0.02/0.05) | 0.01(0/0.02) |
| Incertae_Sedis_XII.*Fusibacter* | 0.011 | <0.01(0/0.02) | 0(0/0) |
| Desulfovibrionaceae.*Desulfovibrio* | 0.013 | <0.01(0/0.22) | 0(0/0) |
| Coriobacteriaceae.unknown_genus | 0.013 | 0.09(0.02/0.26) | 0.02(0.02/0.07) |
| Coriobacteriaceae.*Eggerthella* | 0.013 | 0.02(0.01/0.05) | 0.05(0.02/0.29) |
| Ruminococcaceae.*Oscillibacter* | 0.022 | 2.99(0.93/6.76) | 1.82(0.27/2.46) |
| Peptostreptococcaceae.*Peptostreptococcus* | 0.025 | 0(0/0) | 0(0/0) |
| Incertae_Sedis_XII.unknown_genus | 0.025 | 0(0/<0.01) | 0(0/0) |
| Porphyromonadaceae.unknown_genus | 0.029 | 0.02(0/0.14) | 0(0/<0.01) |
| Prevotellaceae.*Prevotella* | 0.029 | 0.09(0.01/0.73) | 0(0/<0.01) |
| Prevotellaceae.unknown_genus | 0.031 | 0.01(0/0.03) | 0(0/0) |
| Lactobacillaceae.unknown_genus | 0.034 | 0(0/0) | 0(0/0) |
| Veillonellaceae.unknown_genus | 0.035 | 0.05(0.01/0.25) | 0(0/0.01) |
| Ruminococcaceae.*Papillibacter* | 0.036 | 0(0/0) | 0(0/0) |
| Coriobacteriaceae.*Olsenella* | 0.037 | 0(0/0) | 0(0/0) |
| Aerococcaceae.*Abiotrophia* | 0.039 | 0(0/0) | 0(0/0) |
| Verrucomicrobiaceae.*Akkermansia* | 0.039 | 2.62(0.30/7.46) | 1.01(0.09/25.93) |
| Staphylococcaceae.*Staphylococcus* | 0.044 | 0(0/0.01) | 0(0/0) |
| Enterobacteriaceae.unknown_genus | 0.045 | 1.28(0.20/17.98) | 0.42(0.1/2.45) |
| Prevotellaceae.*Paraprevotella* | 0.045 | 0(0/0.36) | 0(0/0) |
| Porphyromonadaceae.*Butyricimonas* | 0.045 | 0(0/0.10) | 0(0/0) |

TABLE 8-continued

Genera having significant difference, relative abundance.

| | | | |
|---|---|---|---|
| Eubacteriaceae.*Eubacterium* | 0.046 | 0.04(0.02/0.12) | 0.15(0.07/0.30) |
| Coriobacteriaceae.*Atopobium* | 0.049 | 0(0/0.01) | 0(0/0) |

(b) Autistic children with/without severe GI problems
(Adjusted P values were 0.313 for all genera)

| Family.Genus | P value | Median (25/75 percentiles) | |
|---|---|---|---|
| | | GI⁻ | GI⁺ |
| Ruminococcaceae.*Acetivibrio* | 0.029 | 0.04(0/0.07) | 0.01(0/0.01) |
| Ruminococcaceae.*Subdoligranulum* | 0.038 | 1.90(0.54/5.26) | 6.21(1.85/17.76) |
| Ruminococcaceae.*Anaerotruncus* | 0.049 | 0.38(0.23/0.62) | 0.81(0.39/1.10) |
| Enterobacteriaceae.unknown_genus | 0.050 | 1.15(0.07/1.86) | 0.29(0.11/11.54) |

Figure 2B:
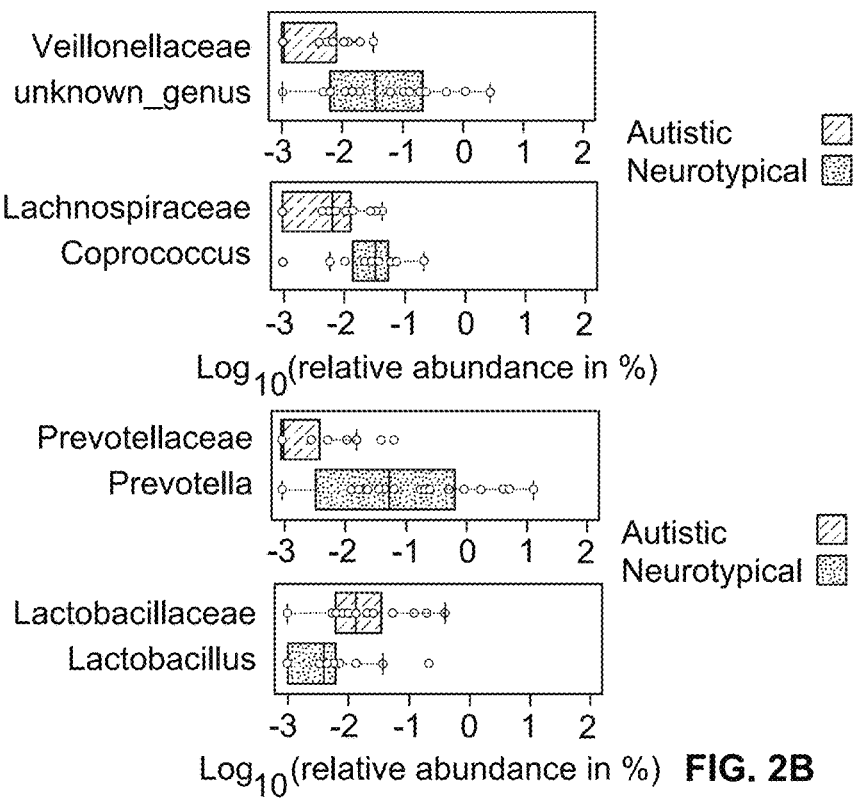
FIG. 2B shows the distribution of 39 subjects based on relative abundance of the 4 most differentially abundant genera for autistic (top box for each genera) and neurotypical (bottom box for each genera) subjects.
Figure 2C:
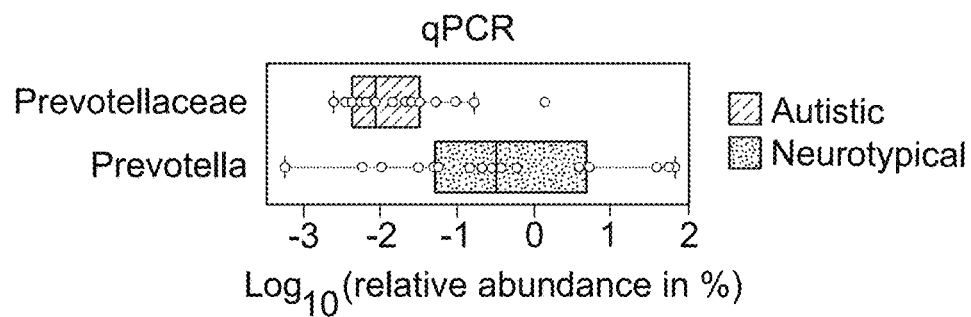
FIG. 2C shows the distribution of 39 subjects based on relative abundance of the genus *Prevotella* obtained by qPCR analysis for autistic (top box for each genera) and neurotypical (bottom box for each genera) subjects.
Figure 2D:
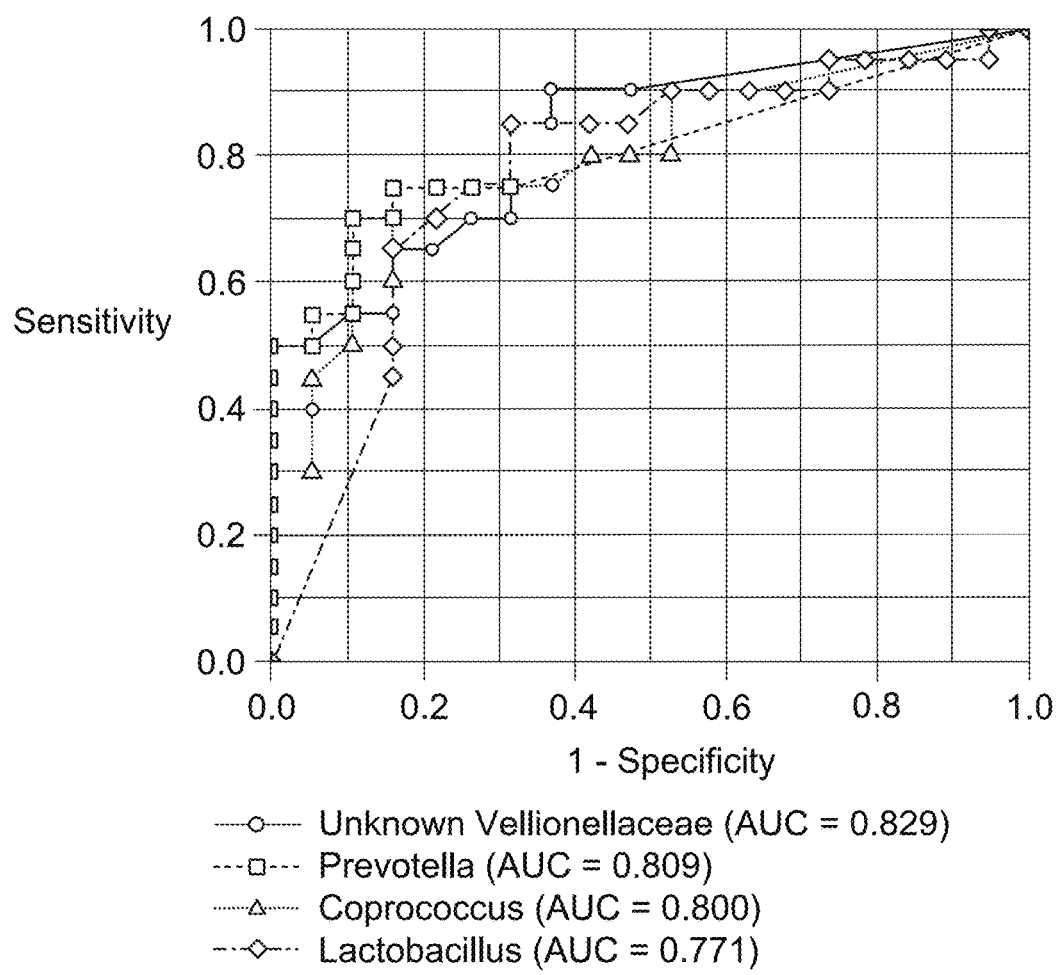
FIG. 2D shows a receiver operating characteristics (ROC) curve of the 4 genera that have the highest area under curve (AUC).

The Mann-Whitney test with multiple testing correction showed that *Prevotella* and unclassified Veillonellaceae were significantly more abundant in the neurotypical group than in the autistic group (adjusted P=0.05, Tables 9 and 10, FIG. 2B). The reduced abundance of *Prevotella* in autistic children was confirmed by use of quantitative real-time PCR (qPCR) (Mann-Whitney test P=0.0002, FIG. 2C).

TABLE 9

By nonparametric rank-sum test (Mann-Whitney test)

(a) top ten differentially abundant genera between neurotypical and autistic children

| Name | P | P adjusted | Median (25%/75%) | |
|---|---|---|---|---|
| | | | Neurotypical | Autism |
| Prevotellaceae.*Prevotella* | 0.000 | 0.050 | 0.09(0.01/0.73) | 0(0/<0.01) |
| Veillonellaceae.unknown_genus | 0.000 | 0.050 | 0.05(0.01/0.25) | 0(0/0.01) |
| Lachnospiraceae.*Coprococcus* | 0.001 | 0.055 | 0.04(0.02/0.05) | 0.01(0/0.02) |
| Prevotellaccae.unknown_genus | 0.001 | 0.055 | 0.01(0/0.03) | 0(0/0) |
| Alcaligenaceae.*Sutterella* | 0.002 | 0.108 | 0.07(0/0.21) | 0(0/0) |
| Lactobacillaceae.*Lactobacillus* | 0.003 | 0.134 | <0.01(0/0.01) | 0.02(0.01/0.05) |
| Porphyromonadaceae.*Butyricimonas* | 0.004 | 0.138 | 0(0/0.10) | 0(0/0) |
| Prevotellaceae.*Prevotella* | 0.004 | 0.140 | 0(0/0.36) | 0(0/0) |
| Incertae_Sedis_XII.*Fusibacter* | 0.005 | 0.144 | <0.01(0/0.02) | 0(0/0) |
| Lachnospiraceae.*Roseburia* | 0.006 | 0.144 | 0.07(0.04/0.21) | 0.03(0.01/0.07) |

(b) differentially abundant genera between autistic children with or without severe GI problems

| Name | P | P adjusted | Median (25%/75%) | |
|---|---|---|---|---|
| | | | GI⁻ | GI⁺ |
| Desulfovibrionaceae.*Desulfovibrio* | 0.036 | 0.462 | 0(0/0.01) | 0(0/0) |
| Alcaligenaceae.*Sutterella* | 0.036 | 0.462 | 0(0/0.03) | 0(0/0) |
| Ruminococcaceae.*Anaerotruncus* | 0.038 | 0.462 | 0.38(0.23/0.62) | 0.81(0.39/1.10) |

TABLE 10

By nonparametric rank-sum test (Mann-Whitney test), differentially abundant genera between neurotypical and autistic children

| Name | P | P adjusted | Median (25%/75%) | |
|---|---|---|---|---|
| | | | Neurotypical | Autism |
| Prevotellaceae.*Prevotella* | 0.000 | 0.050 | 0.09(0.01/0.73) | 0(0/<0.01) |
| Veillonellaceae.unknown_genus | 0.000 | 0.050 | 0.05(0.01/0.25) | 0(0/0.01) |
| Lachnospiraceae.*Coprococcus* | 0.001 | 0.055 | 0.04(0.02/0.05) | 0.01(0/0.02) |
| Prevotellaceae.unknown_genus | 0.001 | 0.055 | 0.01(0/0.03) | 0(0/0) |
| Alcaligenaceae.*Sutterella* | 0.002 | 0.108 | 0.07(0/0.21) | 0(0/0) |
| Lactobacillaceae.*Lactobacillus* | 0.003 | 0.134 | <0.01(0/0.01) | 0.02(0.01/0.05) |
| Porphyromonadaceae.*Butyricimonas* | 0.004 | 0.138 | 0(0/0.10) | 0(0/0) |
| Prevotellaceae.*Prevotella* | 0.004 | 0.140 | 0(0/0.36) | 0(0/0) |
| Incertae_Sedis_XII.*Fusibacter* | 0.005 | 0.144 | <0.01(0/0.02) | 0(0/0) |
| Lachnospiraceae.*Roseburia* | 0.006 | 0.144 | 0.07(0.04/0.21) | 0.03(0.01/0.07) |
| Porphyromonadaceae.unknown_genus | 0.009 | 0.213 | 0.02(0/0.14) | 0(0/<0.01) |
| Staphylococcaceae.*Staphylococcus* | 0.010 | 0.213 | 0(0/0.01) | 0(0/0) |

TABLE 10-continued

By nonparametric rank-sum test (Mann-Whitney test), differentially abundant genera between neurotypical and autistic children

| | | | Median (25%/75%) | |
|---|---|---|---|---|
| Name | P | P adjusted | Neurotypical | Autism |
| Veillonellaceae.*Succinispira* | 0.012 | 0.232 | 0(0/<0.01) | 0(0/0) |
| Eubacteriaceae.*Eubacterium* | 0.016 | 0.259 | 0.04(0.02/0.12) | 0.15(0.07/0.30) |
| Incertae_Sedis_XI.*Parvimonas* | 0.016 | 0.259 | <0.01(0/0.01) | 0(0/0) |
| Aerococcaceae.*Abiotrophia* | 0.017 | 0.259 | 0(0/0) | 0(0/0) |
| Coriobacteriaceae.*Eggerthella* | 0.019 | 0.259 | 0.02(0.01/0.05) | 0.05(0.02/0.29) |
| Desulfovibrionaceae.*Desulfovibrio* | 0.019 | 0.259 | <0.01(0/0.022) | 0(0/0) |
| Desulfovibrionaceae.unknown_genus | 0.021 | 0.259 | 0.02(0.01/0.03) | 0.01(0/0.02) |
| Enterobacteriaceae.*Providencia* | 0.023 | 0.259 | 0(0/0) | 0(0/0) |
| Peptostreptococcaceae.*Peptostreptococcus* | 0.023 | 0.259 | 0(0/0) | 0(0/0) |
| Coriobacteriaceae.*Olsenella* | 0.023 | 0.259 | 0(0/0) | 0(0/0) |
| Lachnospiraceae.*Dorea* | 0.023 | 0.259 | 0.03(0.02/0.10) | 0.02(0.01/0.03) |
| Ruminococcaceae.*Oscillibacter* | 0.024 | 0.259 | 2.99(0.93/6.7) | 1.82(0.27/2.46) |
| Incertae_Sedis_XII.unknown_genus | 0.025 | 0.259 | 0(0/<0.01) | 0(0/0) |
| Veillonellaceae.*Veillonella* | 0.026 | 0.259 | 0.01(0/0.02) | 0.02(0.01/0.07) |
| Coriobacteriaceae.unknown_genus | 0.030 | 0.268 | 0.09(0.02/0.26) | 0.02(0.02/0.07) |
| Neisseriaceae.*Microvirgula* | 0.031 | 0.268 | 0(0/0.01) | 0(0/0) |
| Veillonellaceae.*Allisonella* | 0.034 | 0.268 | 0(0/<0.01) | 0(0/0) |
| Lactobacillaceae.unknown_genus | 0.036 | 0.268 | 0(0/0) | 0(0/0) |
| Ruminococcaceae.*Papillibacter* | 0.036 | 0.268 | 0(0/0) | 0(0/0) |
| Thermoanaerobacteraceae.unknown_genus | 0.044 | 0.268 | 0(0/0) | 0(0/0) |
| Desulfovibrionaceae.*Desulfocurvus* | 0.044 | 0.268 | 0(0/0) | 0(0/0) |
| Spiroplasmataceae.*Spiroplasma* | 0.044 | 0.268 | 0(0/0) | 0(0/0) |

In addition, with marginal statistical significances, the abundance of *Coprococcus* and unclassified Prevotellaceae were also higher in neurotypical samples (adjusted P=0.055, Table 9, FIG. 2B). To measure how correctly two groups of samples could be classified by the relative abundance of each genus, the receiver operating characteristics (ROC) curve was employed, which is closely related to the Mann-Whitney test and commonly used to evaluate the performance of potential biomarkers. The probability of correct prediction by a given binary classifier can be evaluated by measuring the area under curves (AUC) that depict true versus false positives rates, where the AUC value ranges from about 0.5 (random classification) to about 1.0 (perfect classification), as described in Hanley & McNeil, "The meaning and use of the area under a receiver operating characteristic (ROC) curve," 143 Radiol. 29 (1982), which is hereby incorporated by reference in its entirety. The above-mentioned four genera showed the highest AUC values among all genera, at around 0.8 (FIG. 2C and Table 11), which are highly comparable to biomarkers for many clinical disorders, such as for the detection of drug-induced kidney injury and prostate cancer.

TABLE 11

The top 11 genera having the highest area under curves (AUC)

| | | Median (25%/75%) | |
|---|---|---|---|
| Genus Name | AUC | Neurotypical | Autism |
| Veillonellaceae.unknown_genus | 0.812 | 0.05(0.01/0.25) | 0(0/0.01) |
| Prevotellaceae.*Prevotella* | 0.808 | 0.09(0.01/0.73) | 0(0/<0.01) |
| Lachnospiraceae.*Coprococcus* | 0.799 | 0.04(0.02/0.05) | 0.01(0/0.02) |
| Prevotellaceae.unknown_genus | 0.754 | 0.01(0/0.03) | 0(0/0) |
| Lactobacillaceae.*Lactobacillus* | 0.754 | <0.01(0/0.01) | 0.02(0.01/0.05) |
| Alcaligenaceae.*Sutterella* | 0.745 | 0.07(0/0.21) | 0(0/0) |
| Lachnospiraceae.*Roseburia* | 0.739 | 0.07(0.04/0.21) | 0.03(0.01/0.07) |
| Porphyromonadaceae.*Butyricimonas* | 0.712 | 0(0/0.10) | 0(0/0) |
| Porphyromonadaceae.unknown_genus | 0.704 | 0.02(0/0.14) | 0(0/<0.01) |
| Prevotellaceae.*Paraprevotella* | 0.703 | 0(0/0.36) | 0(0/0) |
| Eubacteriaceae.*Eubacterium* | 0.703 | 0.04(0.02/0.12) | 0.15(0.07/0.30) |

Figure 3A:
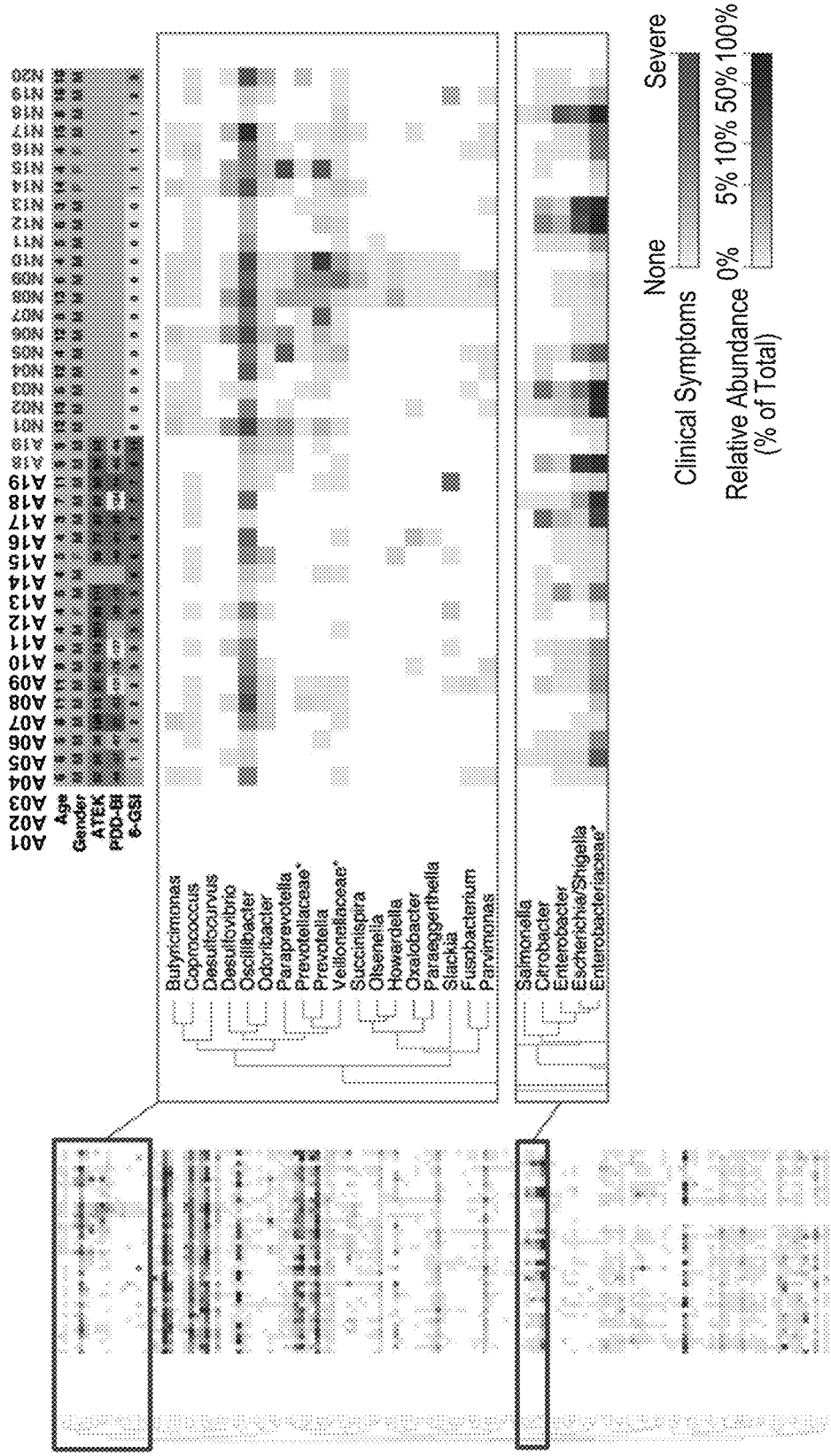
FIG. 3A shows heat map profiles and dendrograms of the all identified genera (A01-A11: autistic children with GI problems; A12-A19: autistic children without GI problems; N01-N20: neurotypical children).
Figure 8A:
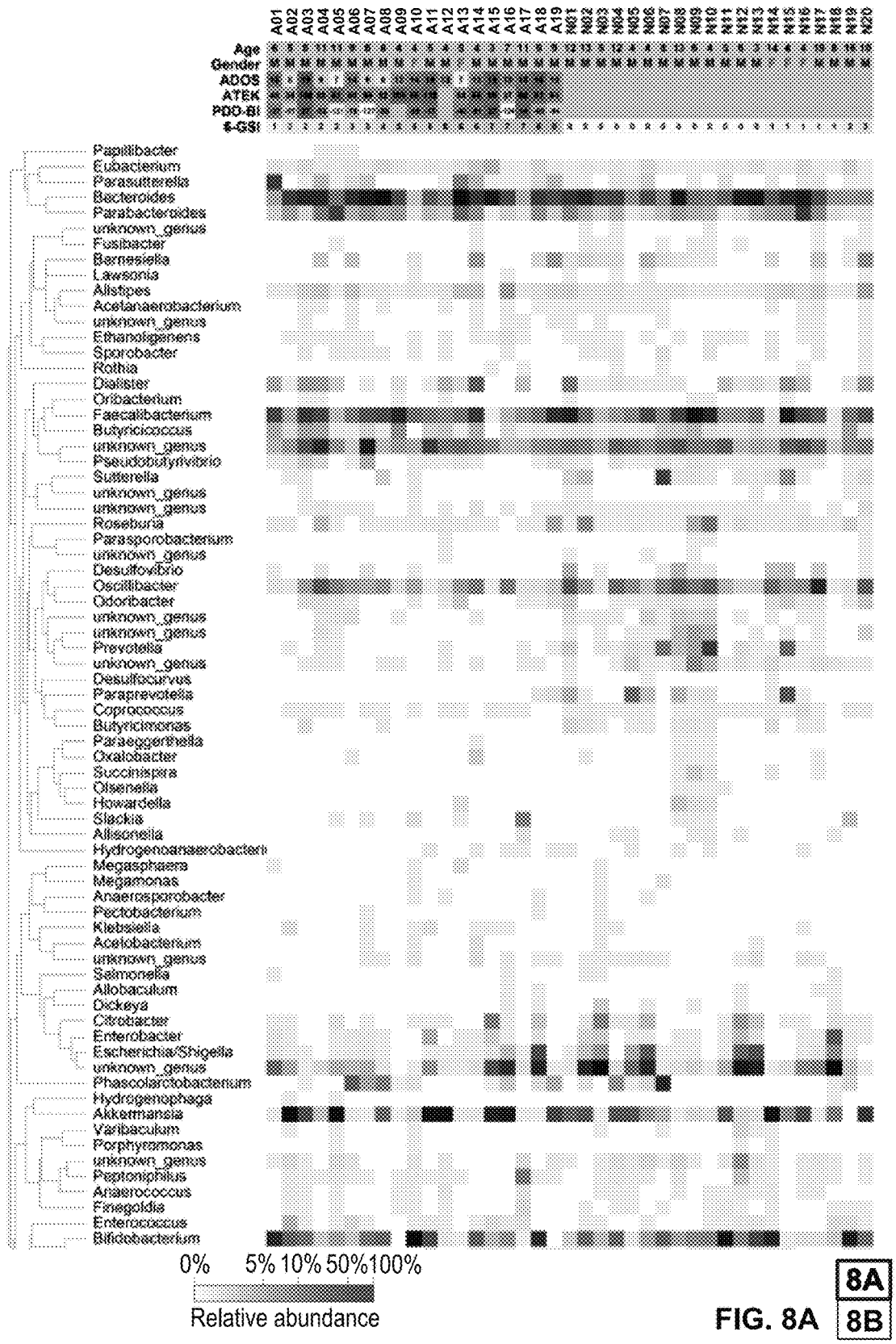
FIG. 8 shows heat map profiles and dendrograms of the all identified genera (A01-A11: autistic children with GI problems; A12-A19: autistic children without GI problems; N01-N20: neurotypical children). A scale bar represents a log scale of the percentile abundance from a total bacteria.
Figure 8B:
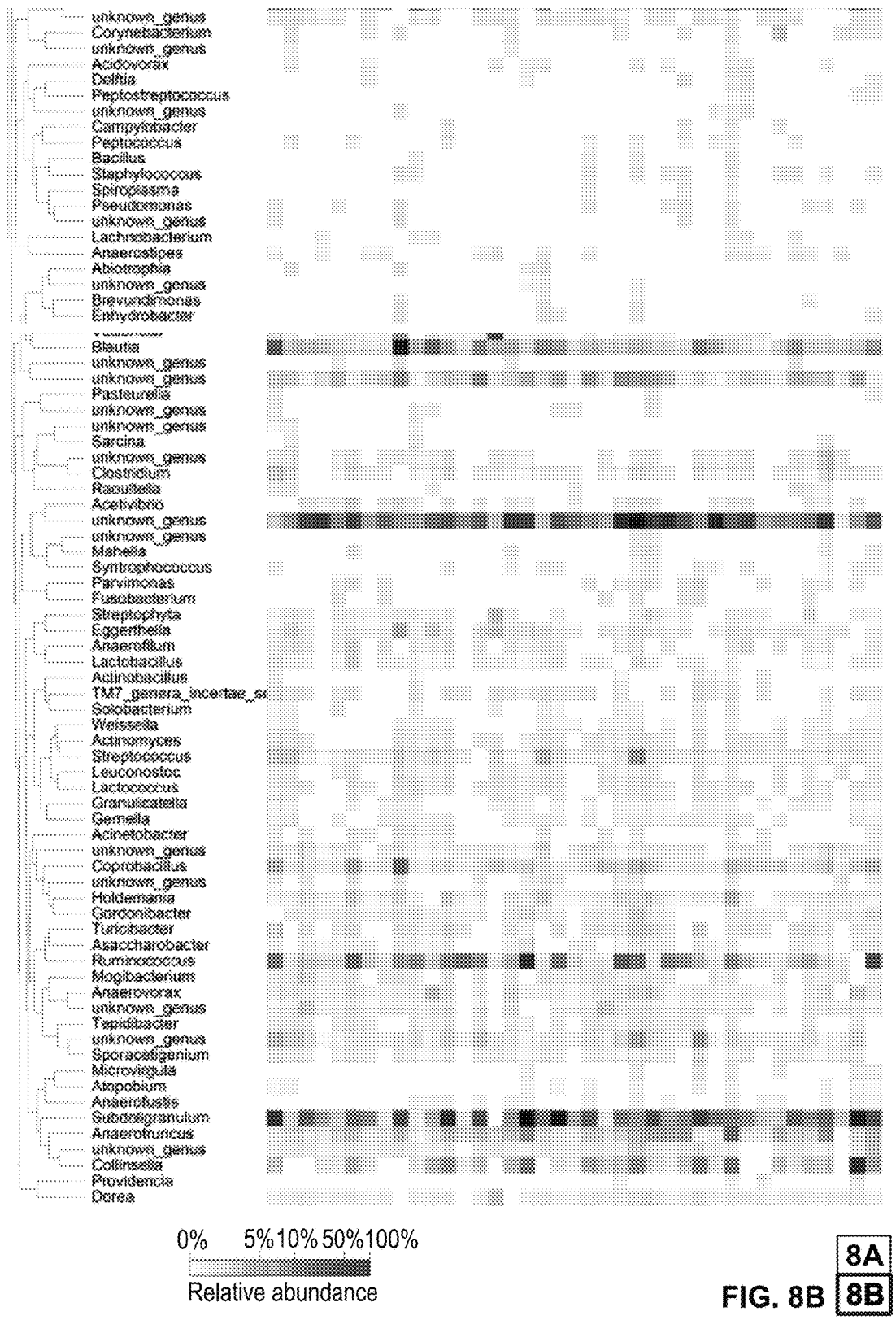

Moreover, the present work revealed autism-associated changes in microbial community profile and enterotypes. Like other environmental microbial ecosystems, human intestinal microflora is distinctively shaped by diverse microorganisms and their mutual interactions. Therefore, autism-related microflora alterations could be found at the level of community, rather than at the individual microbe level. In an effort to identify the systematic differences in microbial communities between neurotypical and autistic groups, all genera were hierarchically clustered based on their relative abundance across samples (FIG. 8). Although the majority of clusters showed no apparent difference between the groups, one cluster of eleven genera that included *Prevotella* were, in general, at a greater abundance in neurotypical samples (FIG. 3A). In addition, these genera shared a similar pattern, especially within neurotypical samples, indicating a coherent relationship among them. Surprisingly, another cluster enriched in Enterobacteriaceae (FIG. 3A) displayed a negatively correlated pattern to the *Prevotella* cluster within the neurotypical group (Pearson/Spearman rank correlation coefficient r=−0.52/−0.67, Fisher transformation test P=0.02/0.001, and permutation test P=0.0002/0.0008). No increase of the Enterobacteriaceae cluster was observed in autistic children, however, despite the significant decrease in *Prevotella*. This suggests that community-wide interrelationship of gut microbiota is generally altered in autistic children.

Principal component analysis (PCA) was performed on 16S rRNA sequencing datasets, and three well-defined 'enterotypes' of human gut microbiota were identified based on the global profiles at the genus level. In addition, the ratio among enterotypes was maintained, regardless of certain disorder conditions, such as obesity and inflammatory bowel disease (IBD), which tend to alter gut microbiota. Notably, *Prevotella* was one of the main classifiers of the three enterotypes, along with *Bacteroides* and *Ruminococcus*. Moreover, a similar co-occurrence pattern to the present data, in which *Desulfovibrio* and *Veilonella* (as an unidentifiable Veilonellaceae in the cluster, FIG. 3A) co-occurred with *Prevotella*, while *Escherichia/Shigella* showed a negative correlation (FIG. 3A). Therefore, given that *Prevotella* was the main difference between neurotypical and autistic groups, any changes in the enterotype profile associated with autism were analyzed. PCA was performed on all thirty-one samples with the relative abundance of sixteen selected genera (Table 12) that commonly appeared in both studies.

TABLE 12

Bacterial groups in co-occurrence networks of enterotype study
Genus

| | | |
|---|---|---|
| *Akkermansia*† | *Gordonibacter*† | *Prevotella*† |
| *Alkaliphilus* | *Helicobacter* | *Rhodospirillum* |
| *Bacteroides*† | *Holdemania*† | Ruminococcaceae |
| *Catenibacterium* | Lachnospiraceae | *Ruminococcus*† |
| *Clostridiales* | *Lactobacillus* | *Slackia* |
| *Desulfovibrio*† | *Leuconostoc* | *Sphingobacterium* |
| *Dialister*† | *Marvinbryantia* | *Staphytococcus*† |
| *Eggerthella*† | *Methanobrevibacter* | *Subdoligranulum*† |
| *Escherichia/Shigella*† | *Parabacterioides*† | *Symbiobacterium* |
| *Geobacter* | Peptostreptococcaceae | *Veillonella*† |

Figure 3B:
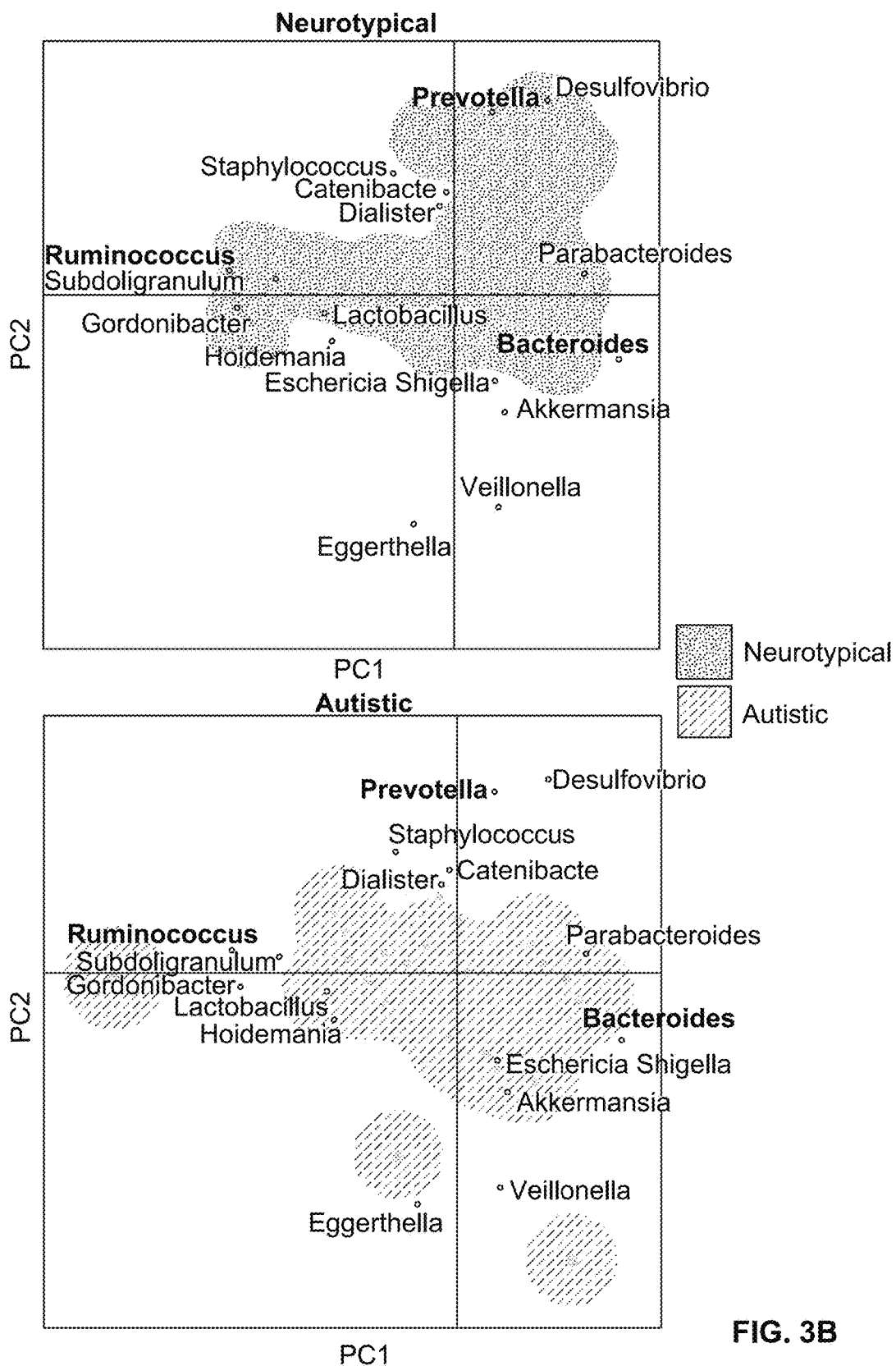
FIG. 3B shows Principal Component Analysis at the genus level from the neurotypical group and the autistic group, both with and without GI problems. Three genera representing enterotypes are identified in bold (*Prevotella, Ruminococcus*, and *Bacteroides*).
Figure 9:
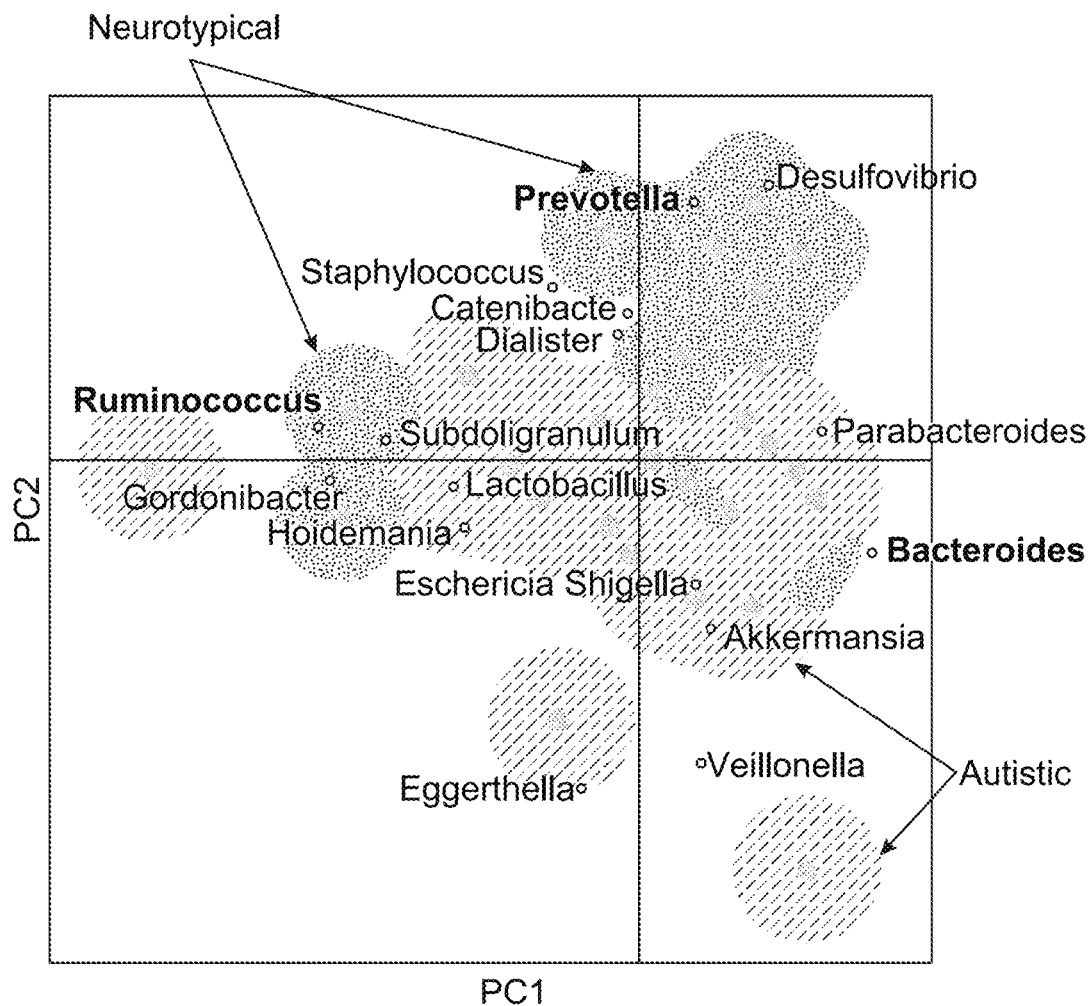
FIG. 9 illustrates an overlapped graph of the Principal Component Analyses of FIG. 3B.

†used for the present PCA analysis. The remaining genera were not considered because of no/little observation through the samples Three core genera of enterotypes (e.g., *Prevotella*, *Bacteroides*, and *Ruminococcus*) were also among the main contributors of the first and the second principal components (FIGS. 3B and 9, Table 13).

TABLE 13

Genera considered for principle component analysis.

| Genera | PC1 | PC2 |
|---|---|---|
| Bacteroidaceae.*Bacteroides* | −0.35† | −0.13 |
| Coriobacteriaceae.*Eggerthella* | 0.08 | −0.48† |
| Coriobacteriaceae.*Gordonibacter* | 0.46† | −0.03 |
| Desulfovibrionaceae.*Desulfovibrio* | −0.19 | 0.40† |
| Enterobacteriaceae.*Escherichia/Shigella* | −0.09 | −0.18 |
| Erysipelotrichaceae.*Catenibacterium* | 0.02 | 0.22 |
| Erysipelotrichaceae.*Holdemania* | 0.26 | −0.10 |
| Lactobacillaceae.*Lactobacillus* | 0.27 | −0.04 |
| Porphyromonadaceae.*Parabacteroides* | −0.27† | −0.04 |
| Prevotellaceae.*Prevotella* | −0.08 | 0.38† |
| Ruminococcaceae.*Ruminococcus* | 0.47† | 0.05 |
| Ruminococcaceae.*Subdoligranulum* | 0.38 | 0.03 |

TABLE 13-continued

Genera considered for principle component analysis.

| Genera | PC1 | PC2 |
|---|---|---|
| Staphylococcaceae.*Staphylococcus* | 0.13 | 0.25 |
| Veillonellaceae.*Dialister* | 0.03 | 0.19 |
| Veillonellaceae.*Veillonella* | −0.09 | −0.44† |
| Verrucomicrobiaceae.*Akkermansia* | −0.11 | −0.24 |

†Main contributors of respective principal component

Surprisingly, when the frequencies of enterotypes were compared between groups, the '*Prevotella*-like enterotype' was absent in the autistic group, while neurotypical samples showed an even distribution among three enterotypes. Furthermore, it appeared that the severity of GI symptoms did not influence the enterotype profile within the autistic group (FIG. 9). Taken together with clustering analyses, these data demonstrate that autistic children have a very distinct gut microbial community structure, which is more profoundly associated with the presence of autistic symptoms than with having GI problems.

Figure 4A:
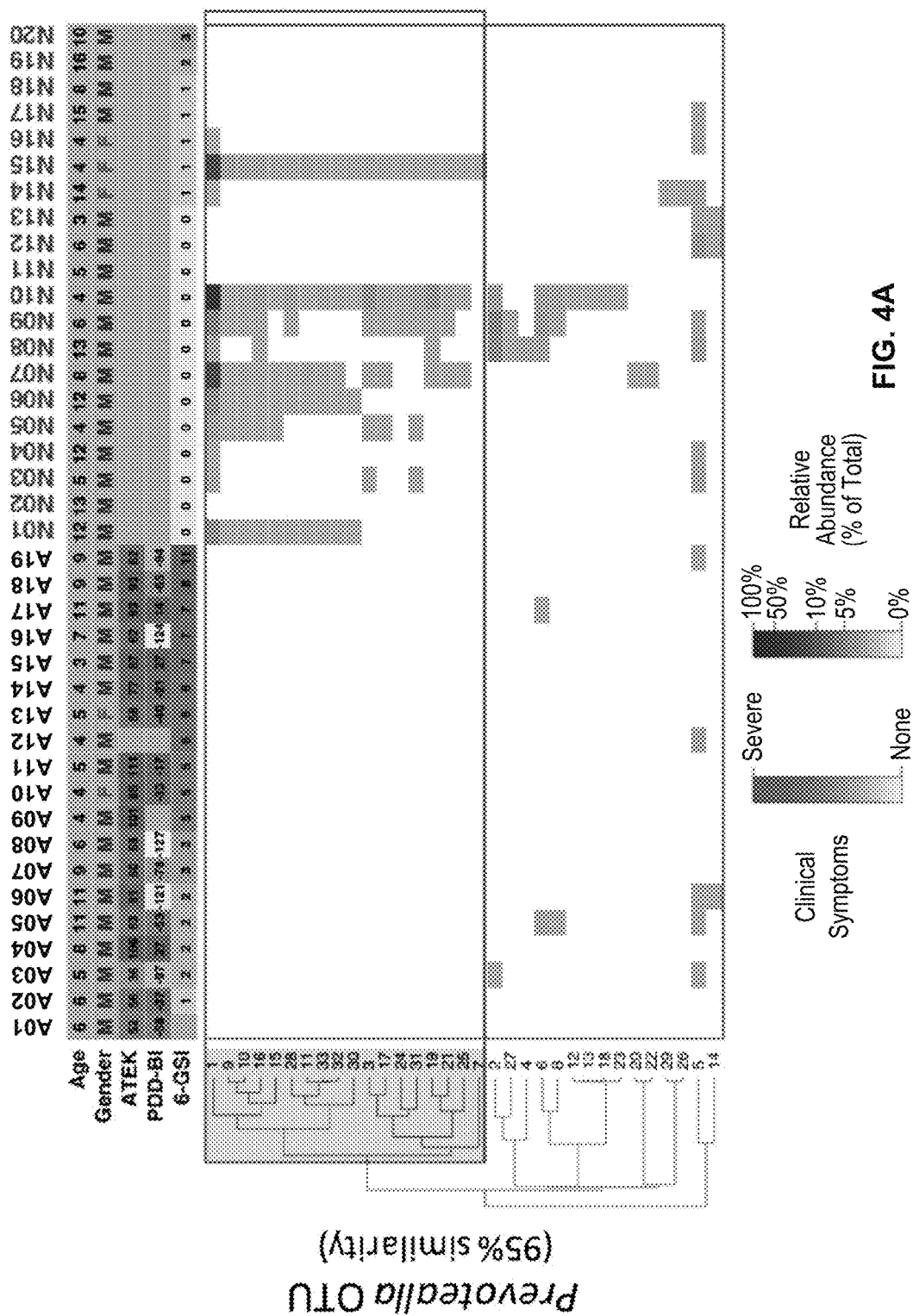
FIG. 4A is a heatmap profile and dendrogram within the genus *Prevotella* (OTUs with 95% threshold) (A01-A11: autistic children with GI problems; A12-A19: autistic children without GI problems; N01-N20: neurotypical children). A scale bar represents a log scale of the percentile abundance from the total bacteria.
Figure 4B:
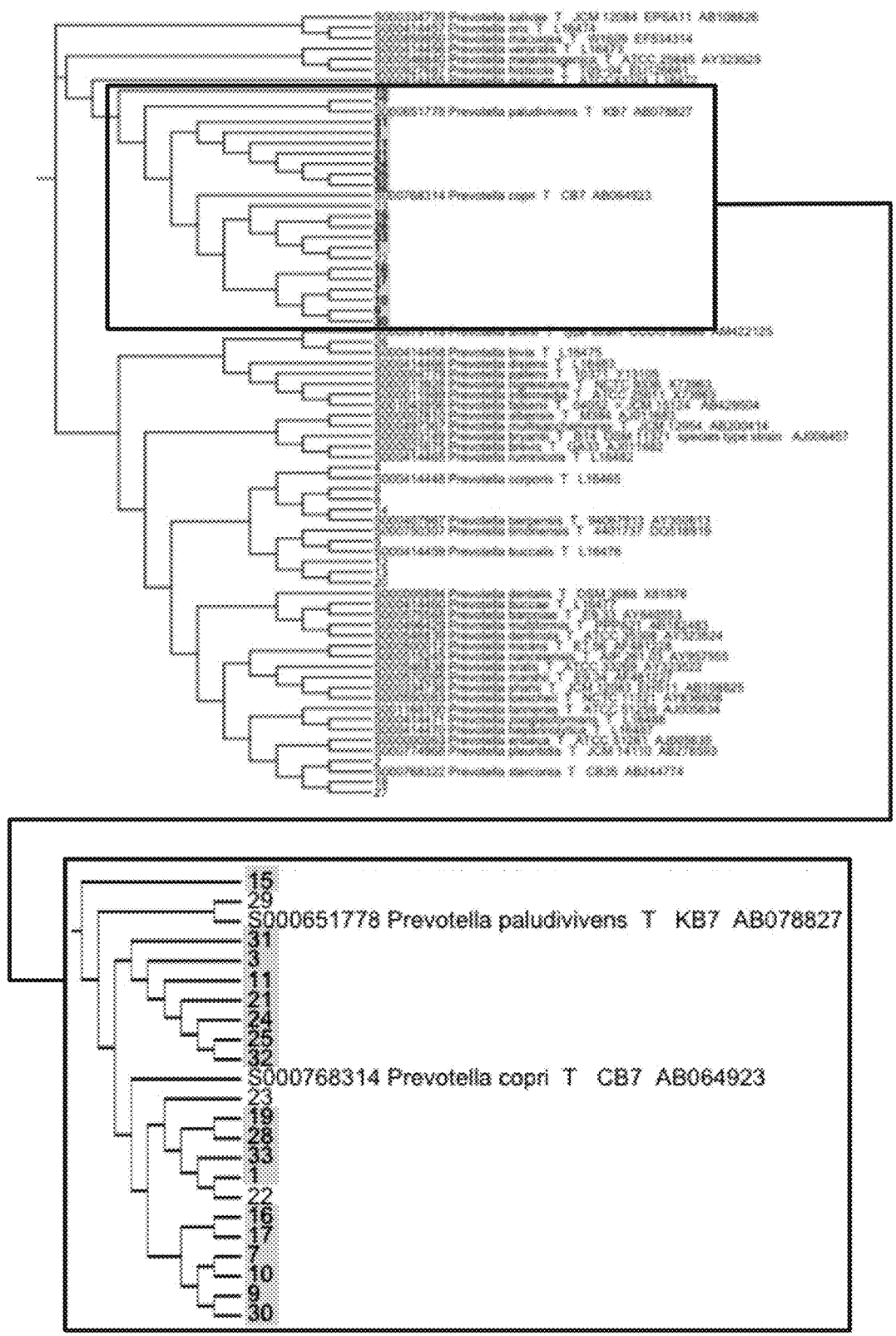
FIG. 4B is a phylogenetic tree within the genus *Prevotella*.

Further characterization of the microbiome included a species-level analysis of *Prevotella*. Most of the 16S rRNA-based metagenomic analyses were done at a genus level due to a low confidence level of classification by using a limited length of sequence reads. Because it is highly likely, however, that a given genus contains multiple species or strains, the genus-level interpretation may suffer intrinsic noise derived from the heterogeneity of data. Therefore, because of the importance of the *Prevotella* genus in the present study, a more in-depth conclusion from the sub-genus level analyses might be inferred. First, all sequences that belonged to *Prevotella* were re-classified into discrete OTUs at an about 95% similarity level by the UCLUST algorithm. The thirty-three identified OTUs were then clustered based on their relative abundance across samples and visualized as a heat map (FIG. 4A). Noticeably, a major cluster of 18 OTUs was exclusively present in neurotypical samples (FIG. 4A), while the other OTUs showed a scattered distribution in both groups. Thus, the *Prevotella* genus in the samples likely consisted of at least two distinct species, and the major cluster of eighteen OTUs dominantly contributed to the abundance difference between neurotypical and autistic groups. In order to see if these OTUs represented any known species, the OTU sequences were then combined with 16S rRNA sequences of forty-two known type-cultured *Prevotella* species, and a phylogenic analysis by multiple alignments was performed. The dendrogram showed that twenty-one *Prevotella* OTUs had higher sequence similarities to *Prevotella copri* and *Prevotella paludivivens* (FIG. 4B). When the OTUs were cross-matched between two independently generated clusters (i.e., based on their relative abundance vs. sequence similarities), surprisingly, all of the eighteen OTUs in the major cluster identified in FIG. 4A were mapped to the sequence cluster that contained *P. copri* and *P. paludivivens* (FIG. 4B). These data strongly suggest that autistic children have significantly low levels of these two or other closely-related *Prevotella* species in their GI tracks, while those species are more frequently found in neurotypical children.

Given the crucial role of gut microorganisms in maintaining GI health, increasing evidence of more frequent occurrence of GI problems in autistic children strongly implies a link between autism and gut microbiota. Although direct causality between autism and GI complications is still unclear, it is important to identify the specific microorganism(s) that can be targeted for diagnosis as well as for treatment of autism-related GI problems and, possibly, other autistic symptoms. As a stepping-stone to reach this long-term goal, the studies described herein compared the composition of intestinal microbiota between neurotypical and autistic children by 16S rRNA-based pyrosequencing and discovered several key differences: (1) autistic children tend to have less a diverse gut microbiome; (2) several individual genera, most notably *Prevotella*, are found at a significantly lower abundance in autistic children; and (3) there are autism-associated global changes (e.g., enterotype profiles) in the intestinal microbial community.

Samples from neurotypical children had higher richness and diversity than the samples from autistic children. As such, higher diversity of gut bacteria may allow better microbial integrity and ability to protect the human intestine from pathogenic gut microbes. It has also been observed in that rural African children tend to have a higher diversity of gut bacteria than European children. It has been hypothesized that the typically fiber-rich diet of African children provided greater resistance to disorders such as diarrhea than the typically lower-fiber diets of European children. A metagenomic analysis showed about 25% fewer genes in the gut of irritable bowel syndrome patients than in the healthy controls. In contrast, a higher diversity has been recorded in children with autism versus neurotypical children. The higher diversity in autistic children was attributed to an increase of pathogenic bacteria. Neurotypical children with higher bacterial richness and diversity are possibly favored, however, by a microbial defense mechanism and may be less vulnerable to bacterial infections that may trigger sudden GI symptoms and neurological problems, such as the increase of anxiety-like behavior by a food-born pathogen.

Through a series of screening tests described herein, a long list of genera was narrowed, and the findings related to the genus *Prevotella* brought worthy insights into the gut microbiota. The detected *Prevotella* species, most closely related to *P. copri* or *P. paludivivens*, were exclusively present in the neurotypical children (FIG. 4B). *Prevotella* was popularized as an oral pathogen and also as a commensal microbe in human large intestines, pig intestines, and the rumen of cattle.

The role of *Prevotella* species in human large intestine has brought more attention because of its ability to degrade a broad spectrum of plant polysaccharides. *Prevotella* species were prevalent in African children who often have a plant-polysaccharide rich diet, which implies that *Prevotella* play a key role in extracting energy from a specific diet. Previous results show that carbohydrate-based diets shift intestinal microbiota towards the *Prevotella*-enterotype. The near absence of *Prevotella* in autistic children suggests that autistic children may have different diet habits, such as less plant-based carbohydrate compared with neutropical subjects (e.g., gluten/casein free diet for autistic children). In fact, autistic children are often known to have significant deficiencies of dissacharides, especially lactase in the upper GI track. In addition, *Prevotella* was one of many dominant gut microbes in individuals whose diets included fish-oil. Fish-oil is a precursor of omega-3 fatty acids, and the high level of omega-3 is helpful to normal brain development. *Prevotella* species may also have a metabolic link to vitamin B1 production, which is beneficial to mitigate ASD because enzymes related to vitamin B1 biosynthesis were overrepresented when *Prevotella* species was enriched. Although these commensal microbes have not been previously linked to autism, the carbohydrate content in diets of autistic children may exert a profound effect on the composition of gut microflora, and, consequently, their GI health. The present disclosure supports a correlation between *Prevotella* and the diets of autistic children.

The prevalence of *Akkermansia* in several autistic subjects also warranted attention (FIG. 7). Although *Akkermansia* is not a generally-known pathogen and is actually considered as a biomarker as a good condition in gut health, it is able to degrade mucins in the large intestine. Therefore, the extremely high abundance of *Akkermansia* may cause increased intestinal permeability and, consequently, a higher chance of developing GI problems such as infection, as previously reported in some children with autism. As discussed herein, a correlation between the abundance of *Akkermansia* and the severity of GI problems was not found.

As presented herein, the cluster analysis and PCA identified a meaningful relation between autism and gut microbe communities. The enterotype approach accounts for the unique position of *Prevotella* in autism-associated changes in gut microflora. Moreover, the network surrounding *Prevotella* species also corresponds to previous human gut studies. In detail, the *Prevotella*-cluster, as shown in FIG. 3, includes a group of noteworthy genera—*Desulfovibrio*, *Oscillibacter*, and *Coprococcus*—that were significantly more abundant in the neurotypical group than in the autistic group. It is contemplated that *Desulfovibria* species may work synergistically with *Prevotella* species to degrade mucin. *Desulfovibrio*, *Prevotella*, and *Oscilibacter* also use microbial exopolysaccharides (EPS) synthesized by *Bifidobacterium* to produce short-chain fatty acids (SCFAs) in the human intestine. *Coprococcus* species are butyrate-producing bacteria that belong to *Clostridium* XIVa of the family Lachnospiraceae, and may be beneficial to sustain mucosal health of neurotypical children. Meanwhile, the Enterobacteriaceae cluster possesses an opposite trend of abundance to the *Prevotella*-cluster among the neurotypical group. The Enterobacteriaceae cluster included several potentially pathogenic genera—*Salmonella*, *Escherichia/Shigella*, and *Citrobacter*—which has appeared along with *Prevotella* species. A significantly low abundance of *Escherichia/Shigella* in African children has generally been observed. The generally low occurrence of GI disorders in African children has been attributed to the suppression of pathogenic *Escherichia/Shigella* by *Prevotella*, and the genus *Escherichia/Shigella* showed a negative correlation with the genus *Prevotella* in the co-occurrence network. This negative correlation disappeared in the autistic group, however, which implicated the possibility of altered microbial networks in the gut of autistic children. Previously, it was found that the core genera of the enterotypes were independent to factors such as body mass index (BMI) and inflammatory bowel disease. Surprisingly, certain enterotypes can be linked to a human disorder, as the present disclosure has done.

The present disclosure also contradicts with studies and general beliefs in the field of neurobiology or nutritional physiology. For example, as described herein, there was no significant difference of Bacteroidetes and Firmicutes between neurotypical and autistic children. Previous studies, on the other hand, reported significantly higher levels of Firmicutes and lower levels of Bacteroidetes in neurotypical children over autistic children. Further, other studies showed an opposite trend in ileum and cecum biopsy samples when they compared neurotypical and autistic children, both with GT problems. Additionally, analysis of biopsy samples revealed the genus *Sutterella* to be predominant in autistic children with GI problems compared to neurotypical children with GI problems. Here, however, a relatively lower abundance of the genus *Sutterella* was found in fecal samples of autistic children compared with neurotypical ones. Differences in sample characteristics (feces versus biopsies), human sampling (subject characteristics), experimental methods (e.g., PCR primer selection), and types of statistical tests used to analyze the data may have affected the results. Thus, the present disclosure has used rigorous correction methods for multiple testing. Pyrosequencing using different primer sets and quantifying genes by quantitative PCR, as shown herein, can fortify the understanding of microbial community.

By way of summary, autistic children have been shown to have distinct gut microflora, which can be characterized by a reduced richness, as well as significant alterations in composition and structure, of the microbial community. Furthermore, gut microbiota seems to have a close association with autistic symptoms but not with GI problems. Notably, the unique absence of *Prevotella* in the autistic group compared to the neurotypical group led suggests *Prevotella* as a potential probiotic or "health specific" biomarker. The list of significant microorganisms determined herein provides a better understanding of the association between gut microbiota and autism and potential targets for diagnosis or treatment.

The present aspects provide for the characterization of the normal flora in the GI tract and/or gut of healthy, neurotypical subjects, and identifying biomarkers for a healthy gut microbiome. In particular, one embodiment provides for the characterization of the gut microbiome in ASD subjects, which microbiome differs from that of neurotypical subjects. Namely, autistic children tend to harbor a unique gut flora compared to neurotypical children, characterized by reduced richness and significant loss of the genus *Prevotella*. In addition to *Prevotella*, the relative abundance of genera *Coprococcus*, Prevotellaceae, and Veillonellaceae were also significantly lower in autistic children than in neurotypical children. Further, *Prevotella*, a versatile carbohydrate-degrading microbe, has been reported as one of the three main classifiers for the human enterotypes, along with *Bacteroides* and *Ruminococcus*. These three core genera were among the main contributors in the principle component analysis. '*Prevotella*-like enterotype' was absent in the autistic group, while neurotypical samples showed an even distribution among three enterotypes, which suggests an altered ability to digest carbohydrates in the autism group.

The present aspects provide for an understanding of the association between gut microbiota, health, and disease states. The present aspects also provide for potential diagnostic and therapeutic targets. More specifically, for example, *Prevotella* can serve as a "healthy gut" biomarker and as a probiotic to improve human gut function and health.

Thus, disclosure one aspect of the processes described herein provides for modifying the intestinal microbiota as a means to establish a neurotypical/healthy profile or as a means for alleviating ASD or ASD symptoms, including GI disorders in ASD subjects. In some aspects, a probiotic therapy is administered as An exemplary embodiment that achieves these goals comprises administering to a subject a composition comprising *Prevotella, Coprococcus*, Prevotellaceae, and/or Veillonellaceae. In some aspects, as a probiotic therapy. Another embodiment provides for the ingestion of prebiotics are ingested in the form of non-digestible foods that support the growth and metabolism of these organisms. For example, *Prevotella* can be obtained, for example, from commercial sources such as the AMERICAN TYPE CULTURE COLLECTION® (ATCC, Manassas, Va.) and cultured anaerobically, e.g., in tryptone-based media, or grown in a ruminant gut and harvested therefrom. *Prevotella* may be provided as a probiotic in means as known in the art, for example, as described in Vidhyalakshmi et al., "Encapsulation 'The Future of Probiotics'—A Review," 3 Adv. Biol. Res. 96 (2009), which is hereby incorporated by reference in its entirety.

Another embodiment provides for the act of ingesting agents (such as antibiotics) that affect the microbiota of the gut. For example, agents that inhibit the growth of microbes present in the ASD microbiome at levels higher than those found in the neurotypical microbiome may be administered. If agents of sufficient specificity are not available, broad spectrum antibiotics may be used in conjunction with probiotic therapy to disrupt the flora of the ASD subject and repopulate the gut with neurotypical flora. In other words, broad-spectrum antibiotics of may be used where probiotics are reintroduced either concurrently, regularly, or subsequently to replace the bacteria killed by the antibiotics. An example antibiotic is the semisynthetic, rifamycin-based, non-systemic antibiotic rifaximin (XIFAXAN®, Salix Pharmaceuticals, Inc., Morrsiville, N.C.), that is essentially non-absorbed from the gut and is being employed for certain gastrointestinal problems. The antibiotic therapy may be long-term or short-term, depending on the maintenance or establishment of the desired microbiota or the obesity management goals of the subject in consultation with the physician. The efficacy of this approach may be monitored by known laboratory and clinical techniques, and may be adjusted accordingly. Other agents that target specific enzymes or pathways of target bacteria include iRNAs, small molecules, combinations thereof, or the like.

As used herein, the terms "treating," "treatment", and "to treat" are used to indicate the production of beneficial or desired results, such as to alleviate symptoms, or eliminate the causation of a disease or disorder (either on a temporary or a permanent basis), slow the appearance of symptoms and/or progression of the disorder, and/or prevent progression of disease. For methods of prevention, a subject to be administered the treatment (e.g., probiotic therapy) is generally a subject having ASD or at risk for ASD and/or pure gut health. The terms "treat" or "treatment" may refer to both therapeutic treatment and prophylactic or preventative measures, wherein the object is to prevent or slow the development of ASD-gut related symptoms. Beneficial or desired clinical results include, but are not limited to, alleviation of symptoms, diminishment of extent of autism, stabilized (i.e., not worsening) state of the ASD-gut-related or GI involvement, delay, or slowing of disease progression, amelioration or palliation of the disease state.

Additionally, therapy or treatment can be measured by monitoring the intestinal biome and/or monitoring the organisms identified herein as associated with ASD versus neurotypical flora. Such an "effective regimen" may be administered over an effective course (a sufficient treatment and/or amount of treatment over a sufficient period of time) to achieve a microbial biome in the body sufficient for increasing bacteria (e.g., *Prevotella*) identified herein as a biomarker of neurotypical flora lacking in ASD subjects or to reduce the relative concentration of bacteria identified as increased in ASD subjects.

The examples below are intended to illustrate the embodiments of the present invention to one of ordinary skill in the art and should not be interpreted as limiting the scope of the invention set forth in the claims.

EXAMPLES

Example 1

Subject Recruitment and Characteristics

Fifty-six (56) applicants, which included thirty (30) neurotypical and twenty-six (26) autistic subjects ranging from 3 to 15 years of age, were enrolled. Neurotypical children that were first-degree relatives of children with ASD were excluded. The twenty-six children with Autism Spectrum Disorders (ASD) were assessed with the Autism Diagnostics Interview Revised (ADI-Revised) and the Autism Diagnostics Observation Schedule (ADOS) to confirm their autism diagnosis. The Autism Treatment Evaluation Checklist (ATEC) and Pervasive Developmental Disorder Behavior Inventory (PDD-BI) assessments were also used to evaluate autism severity. The ATEC consists of four subscales: (1) speech/language/communication; (2) sociability; (3) sensory/cognitive awareness; and (4) health/physical behavior. The total ATEC score is the sum of the scores from each subscale. For PDD-BI scores, a modified "Autism Composite" was determined based on the addition of scores from three subscales-"sensory/perceptual approach behaviors," "ritualisms/resistance to change," and "social pragmatic problems." Scores from "social approach behaviors" and "expressive language" were then subtracted. Higher ATEC and PDD-BI scores indicate more severe ASD.

Also assessed were the gastrointestinal symptoms of the children with a modified version of the Gastro-Intestinal Severity index (GSI) questionnaire. The GSI subscales included six categories of symptoms (constipation, diarrhea, stool consistency, stool smell, flatulence, and abdominal pain). Each category had a 3-point scale and summed up the points to get the total six GI Severity Index (6-GSI). The excluded subscales were "unexplained daytime irritability," "nighttime awakening," and "abdominal tenderness."

Out of the initial twenty-six autistic subjects enrolled, six children were excluded from the further data evaluation: (1) two children who did not meet the ADOS criteria described above; (2) two children who received antibiotic/antifungal treatment during the previous month; (3) one child who did not sufficiently submit required information; and (4) one child who dropped out. Out of the initial thirty neurotypical subjects enrolled, one subject was excluded because of improper sample shipment, and nine female children were not included to balance the number of gender with autistic children. The final forty participants are listed in the Table 14 below.

Example 2

Sample Collection and DNA Extraction

Parents collected and froze a single fecal sample from each subject. Frozen fecal samples were shipped overnight to Arizona State University with a cold pack, and stored in a temperature of about 80° C. until DNA extraction. Genomic DNA was isolated from human stool samples (wet weight: about 1.0 g) using QIAamp DNA Stool Mini Kit (Qiagen, CA) following the manufacturer's instructions. The quantity and quality of DNA were assessed by measuring the absorbance at about 260 nm and about 280 nm using a NanoDrop ND-1000 spectrophotometer (NanoDrop Technology, Rockland, Del.) and agarose gel (about 1%, w/v) electrophoresis.

Example 3

Pyrosequencing Analysis of Community Structures

Extracted genomic DNA was processed at the Research and Testing Laboratory (Lubbock, Tex.), where the bacterial tag-encoded FLX amplicon pyrosequencing (bTEFAP) was performed by the Genome Sequencer FLX-Titanium System and its Titanium protocol (Roche, Indianapolis, Ind.), as described in Sun et al., in "Tag-Encoded FLX Amplicon Pyrosequencing for the Elucidation of Microbial and Functional Gene Diversity in Any Environment" METHS. MOLEC. BIO. 129, which is hereby incorporated by reference for its methods and analysis of pyrosequencing. Bacterial primers 104F (5'-GGCGVACGGGTGAGTAA-3') (SEQ ID NO:1) and 530R (5'-CCGCNGCNGCTGGCAC-3') (SEQ ID NO:2) were used to amplify the combined V2 and V3 regions of 16S rRNA, and the amplicon was sequenced by the procedure described in Wolcott et al., "Evaluation of the bacterial diversity among and within individual venous leg ulcers using bacterial tag-encoded FLX and Titanium amplicon pyrosequencing and metagenomic approaches," 9 BMC Microbiol. (2009), which is hereby incorporated by reference in its entirety. Unqualified sequences were eliminated as described in Garcia-Peña et al., "Anaerobic digestion and c-digestion processes of vegetable and fruit residue," 102 Bioresource Tech. 9447 (2011), which is hereby incorporated by reference in its entirety, and after excluding sequences shorter than 200 bp, about one million non-chimeric sequences, in total, from all forty samples, were obtained, and most samples yielded more than 20,000 sequences (Table 15). It is contemplated that other sequences may be used. Such sequences are available from publicly available resources such as the Green Genes database available at greengenes.lbl.gov:

TABLE 14

Characterization of participants

|  | Neurotypical | Autism-GI⁻ | Autism-GI⁺ |
|---|---|---|---|
| Total # participants | 20 | 12 | 8 |
| Male/Female | 17/3 | 11/1 | 7/1 |
| Age (years) | 8.3 ± 4.4 | 7.5 ± 3.4 | 6.5 ± 2.9 |
| ATEC | — | 71.5 ± 24.2 | 72.1 ± 21.8 |
| PDD-BI | — | −56 ± 46.8 | −43.3 ± 55.2 |
| 6-GSI | 0.5 ± 0.8 | 3.1 ± 1.4 | 7.0 ± 1.1 |

Autism-GI⁻ autistic children with severe GI problems;
Autism-GI⁺ autistic children without severe GI problems

TABLE 15

High-throughput pyrosequencing data summary and OTUs defined by 95% similarity.

| Subject ID | Subject description | Total sequences # | Qualified sequences # | OTUs | Chao1 estimate |
|---|---|---|---|---|---|
| N1 | Neurotypical (N) | 56659 | 27186 | 1116 | 1618 |
| N2 | N | 50072 | 27258 | 784 | 1108 |
| N3 | N | 51837 | 23746 | 1580 | 2439 |
| N4 | N | 57447 | 25463 | 1020 | 1395 |
| N5 | N | 52997 | 21863 | 704 | 1040 |
| N6 | N | 54602 | 21141 | 1313 | 1876 |

TABLE 15-continued

High-throughput pyrosequencing data summary and OTUs defined by 95% similarity.

| Subject ID | Subject description | Total sequences # | Qualified sequences # | OTUs | Chao1 estimate |
|---|---|---|---|---|---|
| N7 | N | 52987 | 26326 | 732 | 960 |
| N8 | N | 79139 | 46701 | 678 | 977 |
| N9 | N | 51470 | 22064 | 1049 | 1377 |
| N10 | N | 53466 | 22213 | 845 | 1136 |
| N11 | N | 63879 | 26188 | 1292 | 1821 |
| N12 | N | 48537 | 21381 | 711 | 980 |
| N13 | N | 35607 | 17156 | 868 | 1293 |
| N14 | N | 53791 | 20094 | 852 | 1108 |
| N15 | N | 47146 | 19328 | 1169 | 1601 |
| N16 | N | 47295 | 25287 | 556 | 701 |
| N17 | N | 75380 | 43412 | 346 | 427 |
| N18 | N | 52168 | 23583 | 514 | 702 |
| N19 | N | 55706 | 27099 | 438 | 598 |
| N20 | N | 52407 | 25617 | 492 | 605 |
| A1 | Autistic without GI problems (A-GI−) | 36430 | 17687 | 428 | 587 |
| A-excl. | A-GI− (excluded subject) | 50829 | 8830 | 176 | 266 |
| A2 | A-GI− | 51190 | 29633 | 860 | 1156 |
| A3 | A-GI− | 49703 | 32744 | 527 | 673 |
| A4 | A-GI− | 44868 | 21717 | 812 | 1086 |
| A5 | A-GI− | 48341 | 19575 | 465 | 641 |
| A6 | A-GI− | 60063 | 24336 | 434 | 557 |
| A7 | A-GI− | 49571 | 15991 | 614 | 816 |
| A8 | A-GI− | 43171 | 16267 | 627 | 826 |
| A9 | A-GI− | 59110 | 30088 | 886 | 1241 |
| A10 | A-GI− | 53074 | 20344 | 462 | 627 |
| A11 | A-GI− | 55065 | 29424 | 593 | 717 |
| A12 | Autistic with GI problems (A-GI+) | 54599 | 25731 | 354 | 411 |
| A13 | A-GI+ | 60877 | 28639 | 856 | 1256 |
| A14 | A-GI+ | 60902 | 28284 | 1066 | 1503 |
| A15 | A-GI+ | 59135 | 30979 | 747 | 973 |
| A16 | A-GI+ | 55105 | 27784 | 488 | 646 |
| A17 | A-GI+ | 48550 | 19213 | 447 | 681 |
| A18 | A-GI+ | 49048 | 20954 | 768 | 1031 |
| A19 | A-GI+ | 58397 | 26475 | 599 | 833 |

To obtain the operational taxonomic units (OTUs), the sequencing readouts were clustered at about 90%, 95%, 97%, and 99% similarity with the UCLUST algorithm described in Edgar, "Search and clustering orders of magnitude faster than BLAST," 26 Bioinformatics 2460 (2010), which is hereby incorporated by reference in its entirety. Thisese percentages are roughly equivalent to the taxonomic terms of family, genus, species, and strain, respectively. Mothur software, described by Schloss et al., "Introducing mothur: Open-Source, Platform-Independent, Community-Supported Software for Describing and Comparing Microbial Communities," 75 Appl. Environ. Microbiol. 7537 (2009), which is hereby incorporated by reference in its entirety, was used to obtain ecological indices of Chao1 estimator and Shannon diversity/richness indices. Finally, sequences were classified by the RDP Classifier software at an about 50%- and about 80%-confidence threshold for sequence length less than about 250 bp and more than about 250 bp, respectively.

Regarding statistical and data analysis, amplicon numbers from each sample were individually normalized to a percentage of total sequences before statistical analyses. Student's t-test and Mann-Whitney test were performed with SciPy library for Python, and the P values were then adjusted for multiple testing by p.adjust function (method=the Benjamini-Hochberg method) in the package that R programming provides (ver.2.11.1). Hierarchical clustering (complete linkage) was performed witha Biopython package, and clustergrams were generated by the Reportlab package for Python (ver.2.6.5). ROC curves and AUC values were obtained using the caTools package in R. Principal, and component analysis was performed using the prcomp function (scaled and centered) in R, from which the coordinates for genus and samples were obtained.

Example 4

Quantitative Real-time PCR Analysis 16S rDNA-targeting quantitative real-time PCR (qPCR) with triplicate PCR reactions in an REALPLEX® 4S Real-Cycler (Eppendorf AG, Hamburg, Germany). were performed For *Prevotella* species, a seven-point standard curve was constructed using genomic DNA of *Prevotella copri* (DSM18205). The PCR reagent mixture for each reaction was about 20 μL of including about 8 μL, of 2.5×SYBR Premix Ex Taq Mix (Takara Bio Inc, Japan), about 1 μL of about 10 μM *Prevotella*-specific forward and reverse primers, as described in Larsen et al., "Gut Microbiota in Human Adults with Type 2 Diabetes Differs from Non-Diabetic Adults."6 Plos One 5 (2010), which is hereby incorporated by reference in its entirety, about 2 μL 10-fold diluted DNA as a template, and about 8 μL PCR grade water. The PCR amplification was conducted with an initial about 10 minute denaturation at about 95° C., followed by about 35 cycles of denaturation (at about 95° C. for about 15 s), and annealing/extension (60° C. about for about 60 s). For general bacteria, qPCR was performed following the protocols described in Ziv-El et al. "Development and characterization of Deha-loR^2, a novel anaerobic microbial consortium performing rapid dechlorination of TCE to ethane," 92 Appl. Microbio. & Biotech. 1063-71 (2011), which is hereby incorporated by reference in its entirety.

Alternative Embodiment A

In at least one embodiment, a method of detecting, in a stool sample, a relative abundance of *Prevotella, Coprococcus*, Prevotellaceae, or Veillonellaceae bacteria that are indicative of autism spectrum disorders (ASD) includes determining the relative abundance of *Prevotella, Coprococcus*, Prevotellaceae, or Veillonellaceae bacteria in the stool sample, wherein a decreased relative abundance of *Prevotella, Coprococcus*, Prevotellaceae or Veillonellaceae bacteria relative to a neurotypical population of said bacteria relative to a neurotypical population of said bacterium, is indicative of pure gut health and/or ASD-gut related problems.

Alternative Embodiment B

In at least one embodiment, a method of detecting, in a stool sample, the relative abundance of *Prevotella*-genus, which is indicative of ASD-gut related problems includes determining the relative abundance of *Prevotella*-genus bacteria in a test stool sample, wherein a decreased relative abundance of *Prevotella*-like enterotype bacteria relative to a neurotypical relative abundance of said bacteria is indicative of ASD.

Alternative Embodiment C

In at least one embodiment, the determining comprises obtaining nucleic acids from said stool sample and sequencing with any deep sequencing technique (e.g., 454 pyrosequencing, illumine, ion torrent) the nucleic acids.

Alternative Embodiment D

In at least one embodiment, the nucleic acids to be sequenced are bacterial 16S rRNA genes.

Alternative Embodiment E

In at least one embodiment, an assay comprises a set of primers that allow for the detection of a relative abundance *Prevotella*-genus in a biological sample. The primers may include, for example, a mixture of primers directed to the 16S rRNA species for *Prevotella* or the like. The absence of *Prevotella*-genus relative to a healthy relative abundance of said bacteria is indicative of poor gut health.

Alternative Embodiment F

In at least one embodiment, a method for quantifying the population of *Prevotella, Coprococcus*, Prevotellaceae, or Veillonellaceae indicative of ASD includes contacting a stool specimen of a subject with a reagent that detects said bacteria. The method further includes detecting a lower relative abundance of said bacteria compared with the relative abundance of said bacteria in a neurotypical sample being indicative of ASD.

Alternative Embodiment G

In at least one embodiment, a method of treating ASD-gut-related symptoms in a subject in need thereof includes assaying a stool sample from said subject for decreased relative abundance of at least one of *Prevotella, Coprococcus*, Prevotellaceae, or Veillonellaceae. The method further includes administering a therapeutically effective amount of probiotic, prebiotic, or pharmaceutical therapy to the subject when the at least one of *Prevotella, Coprococcus*, Prevotellaceae, or Veillonellaceae is lower than an abundance of said bacteria in a neurotypical population of said bacteria.

Alternative Embodiment H

In at least one embodiment, the assay determines relative abundance of at least one of a group comprising *Prevotella, Coprococcus*, Prevotellaceae, or Veillonellaceae.

Alternative Embodiment I

In at least one embodiment, the assay determines relative abundance of at least one of a group consisting essentially of *Prevotella, Coprococcus*, Prevotellaceae, or Veillonellaceae.

Alternative Embodiment J

In at least one embodiment, the assay determines relative abundance of at least one of a group consisting of *Prevotella, Coprococcus*, Prevotellaceae, or Veillonellaceae.

Alternative Embodiment K

In at least one embodiment, the at least one of *Prevotella, Coprococcus*, Prevotellaceae, or Veillonellaceae is at least two of *Prevotella, Coprococcus*, Prevotellaceae, or Veillonellaceae.

Alternative Embodiment L

In at least one embodiment, the at least one of *Prevotella, Coprococcus*, Prevotellaceae, or Veillonellaceae is at least three of *Prevotella, Coprococcus*, Prevotellaceae, or Veillonellaceae.

Alternative Embodiment M

In at least one embodiment, the at least one of *Prevotella, Coprococcus*, Prevotellaceae, or Veillonellaceae is all four of *Prevotella, Coprococcus*, Prevotellaceae, or Veillonellaceae.

Alternative Embodiment N

In at least one embodiment, the assaying comprises sequencing multiple nucleic acid chains concurrently, for example, 16S rRNA sequences from various species. This comprise3s contacting the sample with primers that are specific for each species' 16S rRNA gene as are readily available from the publicly available database Alternative Embodiment O In at least one embodiment, the at least one of *Prevotella, Coprococcus*, Prevotellaceae, or Veillonellaceae is at least one of:
  a. *Prevotella, Coprococcus*, Prevotellaceae, and Veillonellaceae;
  b. *Coprococcus*, Prevotellaceae, and Veillonellaceae;
  c. *Prevotella*, Prevotellaceae, and Veillonellaceae;
  d. *Prevotella, Coprococcus*, and Veillonellaceae;
  e. *Prevotella, Coprococcus*, and Prevotellaceae;
  f. Prevotellaceae and Veillonellaceae;
  g. *Coprococcus* and Veillonellaceae;
  h. *Coprococcus* and Prevotellaceae;
  i. *Prevotella* and Veillonellaceae;
  j. *Prevotella* and Prevotellaceae;
  k. *Prevotella* and *Coprococcus;*
  l. Veillonellaceae;
  m. Prevotellaceae;
  n. *Coprococcus*; or
  o. *Prevotella.*

Alternative Embodiment P

In at least one embodiment, 8. The method of claim 7, further comprising administering an agent to inhibit growth of at least one microorganism in the subject, wherein the microorganism is one having a higher relative abundance in a microbiome of ASD subjects compared with a microbiome of neurotypical subjects.

Alternative Embodiment Q

In at least one embodiment, 9. A method for treating ASD-gut related symptoms/complications in a subject comprising: administering probiotic to said subject, wherein said subject, prior to administration, has tested deficient for *Prevotella*, and/or *Coprococcus*, and/or Prevotellaceae, and/or Veillonellaceae, wherein a deficiency of *Prevotella, Coprococcus*, Prevotellaceae, or Veillonellaceae relative to a neurotypical population of said bacteria is indicative of ASD.

Alternative Embodiment R

In at least one embodiment, 10 A method for treating ASD gut related symptoms in a subject comprising: administering a prebiotic that stimulates the growth of *Prevotella*, and/or *Coprococcus*, and/or Prevotellaceae, and/or Veillonellaceae to said subject, wherein said subject, prior to administration, has tested deficient for *Prevotella*, and/or *Coprococcus*, and/or Prevotellaceae, and/or Veillonellaceae, wherein a deficiency of *Prevotella, Coprococcus*, Prevotellaceae, or Veillonellaceae relative to a neurotypical/healthy population of said bacteria is indicative of pure gut health and/or ASD gut related symptoms/complications.

Alternative Embodiment S

In at least one embodiment, 10. The use of *Prevotella* as biomarker for health of the human gut, wherein the absence or diminished relative abundance of *Prevotella* indicates poor gut health.

Alternative Embodiment T

In at least one embodiment, 11. DNA targeted detection methods for any of the above claims above can be extended to be: qPCR, RT-qPCR, clone libraries, DGGE, T-RFLP, ARISA, microarrays, FIFH, dot-blot hybridization, and any other DNA hybridization methods that will detect a specific sequence in *Prevotella, Coprococcus*, Prevotellaceae, or Veillonellaceae.

Alternative Embodiment U

In at least one embodiment, 12. Protein detection methods for any of the above claims such as 2-Dimensional Gel Electrophoresis (2D-GE), Difference Gel Electrophoresis (2D-DIGE), MALDI TOF-MS, (2D-) LC-ESI-MS/MS, AQUA and iTRAQ, can also be applied to detect multiple or a specific protein in *Prevotella, Coprococcus*, Prevotellaceae, or Veillonellaceae.

The invention claimed is:

1. A method for treating autism spectrum disorder-gut related symptoms/complications in a subject comprising:
    administering a probiotic comprising *Prevotella*, and/or *Coprococcus*, and/or Prevotellaceae, and/or Veillonellaceae to said subject, wherein said subject, prior to administration, has tested deficient for said *Prevotella*, and/or *Coprococcus*, and/or Prevotellaceae, and/or Veillonellaceae.

2. The method of claim 1, further comprising, prior to administration:
    subjecting a nucleic acid sample extracted from the gut of the subject to a genotyping assay that detects at least one of *Prevotella, Coprococcus*, Prevotellaceae, or Veillonellaceae bacteria; and
    measuring a relative abundance of the at least one of *Prevotella, Coprococcus*, Prevotellaceae, or Veillonellaceae bacteria that is below a predetermined abundance to determine that the subject has tested deficient for *Prevotella*, and/or *Coprococcus*, and/or Prevotellaceae, and/or Veillonellaceae.

3. The method of claim 2, wherein the predetermined abundance is a neurotypical amount.

4. The method of claim 2, wherein the assay detects at least two of *Prevotella, Coprococcus*, Prevotellaceae, or Veillonellaceae.

5. The method of claim 2, wherein the subjecting nucleic acid extracted from the subject to a genotyping assay comprises contacting the nucleic acid with at least one primer that specifically binds to 16S rRNA nucleic acid of at least one of *Prevotella, Coprococcus*, Prevotellaceae, or Veillonellaceae.

6. The method of claim 2, further comprising comparing the detected relative abundance of the at least one of *Prevotella, Coprococcus*, Prevotellaceae, or Veillonellaceae bacteria to the predetermined abundance of the at least one of *Prevotella, Coprococcus*, Prevotellaceae, or Veillonellaceae bacteria.

7. The method of claim 2, wherein the determining comprises obtaining nucleic acids from a stool sample and sequencing the nucleic acids with a deep sequencing technique.

8. The method of claim 7, wherein the nucleic acids to be sequenced are bacterial 16S rRNA genes.

9. The method of claim 1, further comprising, prior to administration:
    subjecting protein extracted from a test sample of the subject to a protein assay that determines at least one protein indicative of at least one of *Prevotella, Coprococcus*, Prevotellaceae, or Veillonellaceae bacteria, the test sample including microbiota from a gut of the subject; and
    determining a relative abundance of the at least one of *Prevotella, Coprococcus*, Prevotellaceae, or Veillonellaceae bacteria that is below a predetermined abundance to determine that the subject has tested deficient for *Prevotella*, and/or *Coprococcus*, and/or Prevotellaceae, and/or Veillonellaceae.

10. The method of claim 9, wherein the protein assay includes at least one of 2-Dimensional Gel Electrophoresis, 2-Diminsional Difference Gel Electrophoresis (2D-DIGE), MALDI TOF-MS, (2D-) LC-ESI-MS/MS, AQUA, and iTRAQ.

11. The method of claim 9, further comprising comparing the detected relative abundance of the at least one of *Prevotella, Coprococcus*, Prevotellaceae, or Veillonellaceae bacteria to the predetermined abundance of the at least one of *Prevotella, Coprococcus*, Prevotellaceae, or Veillonellaceae bacteria.

12. The method of claim 9, wherein the determining comprises obtaining nucleic acids from a stool sample and sequencing the nucleic acids with a deep sequencing technique.

13. The method of claim 12, wherein the nucleic acids to be sequenced are bacterial 16S rRNA genes.

14. The method of claim 9, further comprising administering an agent to inhibit growth of at least one microorganism in the subject, wherein the microorganism is one having a higher relative abundance in the microbiome of autism spectrum disorder subjects compared with the microbiome of neurotypical subjects.

* * * * *